United States Patent
Vakoc et al.

(10) Patent No.: US 12,222,202 B2
(45) Date of Patent: Feb. 11, 2025

(54) SYSTEMS, METHODS, AND MEDIA FOR MULTIPLE BEAM OPTICAL COHERENCE TOMOGRAPHY

(71) Applicant: The General Hospital Corporation, Boston, MA (US)

(72) Inventors: Benjamin Vakoc, Arlington, MA (US); Yongjoo Kim, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 239 days.

(21) Appl. No.: 17/757,723

(22) PCT Filed: Dec. 21, 2020

(86) PCT No.: PCT/US2020/066399
§ 371 (c)(1),
(2) Date: Jun. 20, 2022

(87) PCT Pub. No.: WO2021/127636
PCT Pub. Date: Jun. 24, 2021

(65) Prior Publication Data
US 2023/0341222 A1 Oct. 26, 2023

Related U.S. Application Data

(60) Provisional application No. 62/951,710, filed on Dec. 20, 2019.

(51) Int. Cl.
*G01B 9/02091* (2022.01)
*G01B 9/02001* (2022.01)
(Continued)

(52) U.S. Cl.
CPC ..... *G01B 9/02091* (2013.01); *G01B 9/02005* (2013.01); *G01B 9/0201* (2013.01); *G01B 9/02011* (2013.01); *G01B 9/02028* (2013.01)

(58) Field of Classification Search
CPC ............ G01B 9/02091; G01B 9/02005; G01B 9/0201; G01B 9/02011; G01B 9/02028
See application file for complete search history.

(56) References Cited

U.S. PATENT DOCUMENTS 8,605,289 B2   12/2013   Koerner et al.
9,200,888 B2   12/2015   Jaillon et al.
(Continued)

FOREIGN PATENT DOCUMENTS

JP   2001272332 A   10/2001
JP   2016505828 A   2/2016
(Continued)

OTHER PUBLICATIONS

Goetzinger et al. Polarization maintaining fiber based ultra-high resolution spectral domain polarization sensitive optical coherence tomography. Optics Express vol. 17, No. 25, 2009. [retrieved on Feb. 13, 2009). Retrieved from the Internet. <URL: https://www .osapublishing.org/oe/fulltext.cfm?uri=oe-17-25-22704&id=190732>.
(Continued)

*Primary Examiner* — Edmond C Lau
*Assistant Examiner* — Jarreas Underwood
(74) *Attorney, Agent, or Firm* — Quarles & Brady LLP

(57) ABSTRACT

Systems, methods, and media for multiple beam optical coherence tomography are provided which, in some embodiments, include: a light source; a splitter that outputs a fraction of light to various waveguides; optical components that receive light from the waveguides and direct the light as beams that simultaneously impinge a sample at different lateral positions, and collect backscattered light from the lateral positons; another splitter that outputs a fraction of light to waveguides of a reference arm as reference light samples; a mixer that receives the backscattered light samples and the reference light samples, and combines each
(Continued)

backscattered sample with a corresponding reference sample such that the mixer outputs fringes; and a detector that receives the fringes, and outputs OCT signals, each indicative of a structure of the sample at a respective lateral position.

29 Claims, 17 Drawing Sheets

(51) Int. Cl.
  *G01B 9/02002* (2022.01)
  *G01B 9/02015* (2022.01)

(56) References Cited

U.S. PATENT DOCUMENTS

| | | | |
|---|---|---|---|
| 9,400,169 B2* | 7/2016 | Zhou | A61B 5/0066 |
| 10,533,837 B2 | 1/2020 | Frisken | |
| 2006/0103850 A1* | 5/2006 | Alphonse | A61B 5/0066 |
| | | | 356/479 |
| 2007/0236700 A1* | 10/2007 | Yun | G01N 21/4795 |
| | | | 356/477 |
| 2011/0075153 A1 | 3/2011 | Hogan | |
| 2012/0188555 A1* | 7/2012 | Izatt | G01B 9/02078 |
| | | | 356/479 |
| 2014/0118748 A1 | 5/2014 | Rubio Guivernau et al. | |
| 2016/0045106 A1* | 2/2016 | Jaillon | G01B 9/02019 |
| | | | 351/221 |
| 2019/0049232 A1* | 2/2019 | Vakoc | H01S 3/0675 |

FOREIGN PATENT DOCUMENTS

| | | |
|---|---|---|
| JP | 2016031294 A | 3/2016 |
| JP | 2019510962 A | 4/2019 |
| WO | 2017013177 A1 | 1/2017 |
| WO | 2018209339 A1 | 11/2018 |
| WO | 2019084610 A1 | 5/2019 |

OTHER PUBLICATIONS

PCT/US2020/066399—International Search Report and Written Opinion—Mar. 24, 2021.

T. Klein, W. Wieser, C. M. Eigenwillig, B. R. Biedermann, and R. Huber, "Megahertz OCT for ultrawide field retinal imaging with a 1050 nm Fourier domain mode-locked laser," Opt Express 19, 3044-3062 (2011).

B. M. Potsaid, V. Jayaraman, J. G. Fujimoto, J. Jiang, P. Heim, and A. E. Cable, "MEMS tunable VCSEL light source for ultrahigh speed 60kHz-1MHz axial scan rate and long range centimeter class OCT imaging," Proc. SPIE 8213, 9 (2012).

S. Tozburun, M. Siddiqui, and B. J. Vakoc, "A rapid, dispersion-based wavelength-stepped and wavelength-swept laser for optical coherence tomography," Opt. Express 22, 3414-3424 (2014).

Y. Luo, L. J. Arauz, J. E. Castillo, J. K. Barton, and R. K. Kostuk, "Parallel optical coherence tomography system," Appl Opt 46, 8291-8297 (2007).

W. Wieser, B. R. Biedermann, T. Klein, C. M. Eigenwillig, and R. Huber, "Multi-megahertz OCT: High quality 3D imaging at 20 million A-scans and 4.5 GVoxels per second," Opt Express 18, 14685-14704 (2010).

C. Zhou, A. Alex, J. Rasakanthan, and Y. Ma, "Space-division multiplexing optical coherence tomography," Opt Express 21, 19219-19227 (2013).

Y. Huang, M. Badar, A. Nitkowski, A. Weinroth, N. Tansu, and C. Zhou, "Wide-field high-speed space division multiplexing optical coherence tomography using an integrated photonic device," Biomed Opt Express 8, 3856-3867 (2017).

C. Jun, M. Villiger, W. Y. Oh, and B. E. Bouma, "All-fiber wavelength swept ring laser based on Fabry Perot filter for optical frequency domain imaging," Opt Express 22, 25805-25814 (2014).

A. Galtarossa, C. G. Someda, A. Tommasini, B. A. Schrefler, G. Zavarise, and M. Schiano, "Stress distribution in optical-fiber ribbons," IEEE Photonics Technology Letters 9, 354-356 (1997).

Ren, H. et al., Phase-Resolved Polarization Sensitive Optical Coherence Tomography Imaging of Tendon and Muscle, Coherence Domain Optical Methods and Optical Coherence Tomography in Biomedicine VII, Proceedings of SPIE, 2003, 4956:320-328.

European Patent Office, Extended Search Report, Application No. 20903639.1, Dec. 19, 2023, 9 pages.

\* cited by examiner

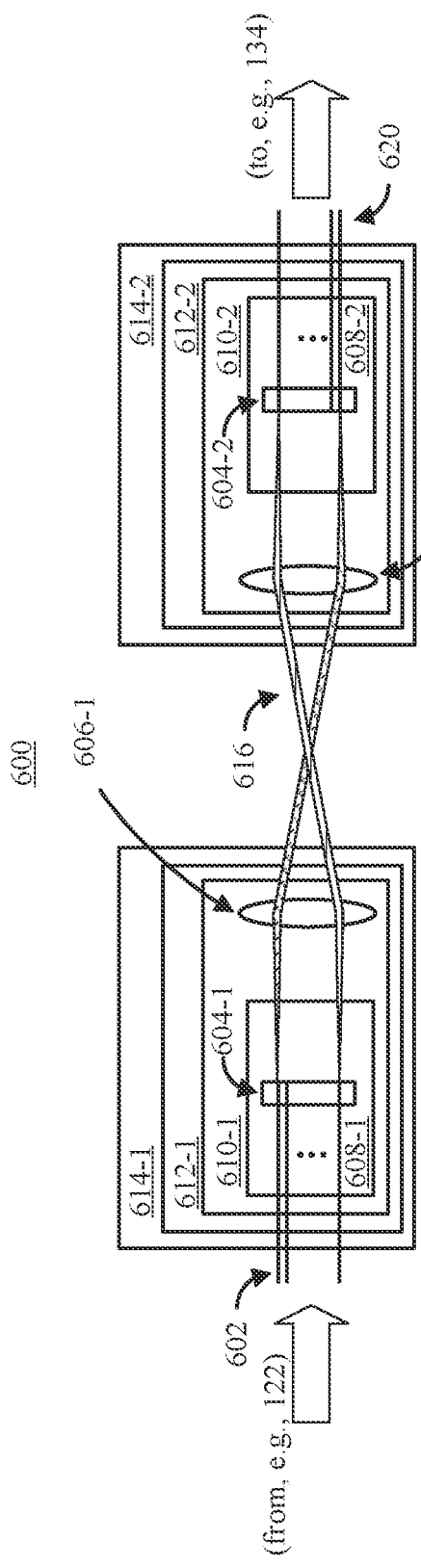
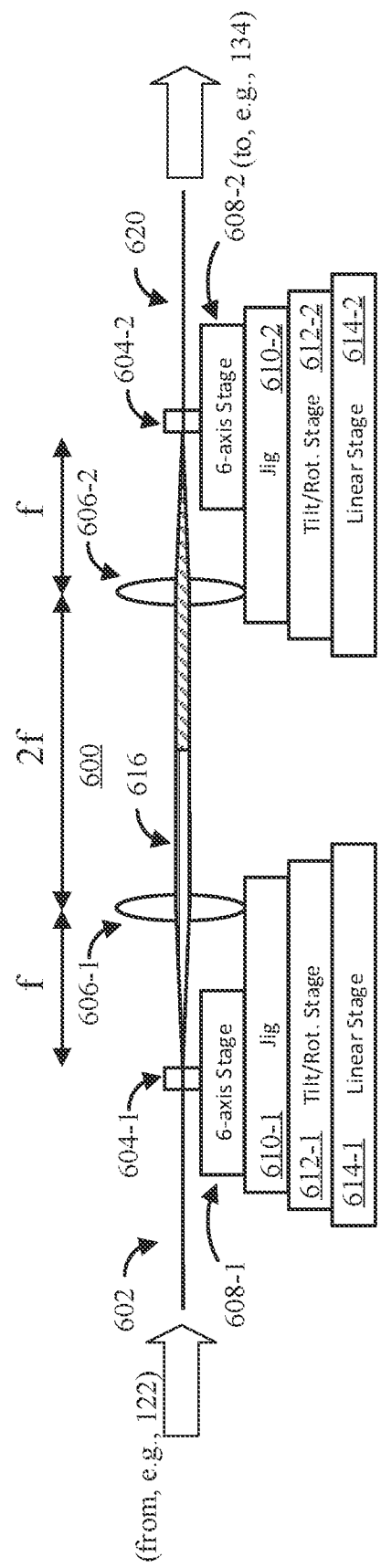
FIG. 6A
FIG. 6B

SYSTEMS, METHODS, AND MEDIA FOR MULTIPLE BEAM OPTICAL COHERENCE TOMOGRAPHY

CROSS REFERENCE TO RELATED APPLICATIONS

This application represents the U.S. national stage entry of PCT International Application No. PCT/US2020/066399, filed Dec. 21, 2020, which is based on, claims the benefit of, and claims priority to U.S. Provisional Application No. 62/951,710, filed Dec. 20, 2019, each of which are hereby incorporated herein by reference in their entirety for all purposes.

STATEMENT REGARDING FEDERALLY SPONSORED RESEARCH

This invention was made with government support under grant number P41EB015903 awarded by the National Institutes of Health. The government has certain rights in the invention.

BACKGROUND

In general, the imaging speed of an optical coherence tomography (OCT) system is directly correlated with performance of the OCT system. By increasing imaging speeds, OCT systems are able to interrogate larger areas, accommodate sample motion, and implement oversampling techniques that enable angiographic contrast. An intuitive approach to increasing OCT imaging speed is to increase the increase the sweep speed of the light source in swept-wavelength-based OCT systems. However, efforts to extend sampling speeds beyond 1 megahertz (MHz) have proven challenging.

Another approach to increasing the effective sampling speed of the system is to increase the number of beams and/or use an extended beam in which a number of lateral positions are imaged simultaneously by a set of beams and/or a beam that extends laterally along the sample. In such an approach, the lateral positions are detected simultaneously using parallel imaging channels, which allows for effectively higher imaging rates by capturing the information from the multiple beams and/or extended beam.

Past efforts to increase the number of beams have utilized separate interferometers for each imaging channel, which limits the scalability of this approach to only a few channels and increases system complexity. Other efforts have attempted to use a multibeam interferometer using integrated photonic devices, but precise control of optical delays for each channel requires extensive manual efforts and/or micro-fabrication of the devices to depth-encode the channel information.

Accordingly, new systems, methods, and media for multiple beam optical coherence tomography are desirable.

SUMMARY

In accordance with some embodiments of the disclosed subject matter, systems, methods, and media for multiple beam optical coherence tomography are provided.

In accordance with some embodiments, of the disclosed subject matter, a system for multiple beam optical coherence tomography is provided, the system comprising: a sample arm optically configured to be coupled to a light source, the sample arm comprising: a first optical fiber comprising a proximal end optically coupled to the light source and a distal end, a first splitter optically coupled to the distal end of the first optical fiber and optically coupled to a proximal end of each of a first plurality of optical fibers, wherein the first plurality of optical fibers comprises n optical fibers, and a first plurality of optical components configured to: receive from the plurality of optical fibers a respective plurality of beams, cause the plurality of beams to be emitted toward a sample, receive a plurality of backscattered light samples from the sample, wherein the plurality of backscattered light samples are spatially separated, and wherein each of the plurality of backscattered light samples corresponds to one of the first plurality of beams, and direct the plurality of backscattered light samples toward a detector; a reference arm optically coupled to the light source, the reference arm comprising: a second optical fiber comprising a proximal end optically coupled to the light source and a distal end, and a second splitter optically coupled to the distal end of the second optical fiber and optically coupled to a proximal end of each of a second plurality of optical fibers, wherein the second plurality of optical fibers comprises n optical fibers; a second plurality of optical components configured to: combine each of the plurality of backscattered light samples with a beam emitted by a corresponding optical fiber of the second plurality of optical fibers yielding a plurality of fringes, and direct each of the plurality of fringes to a corresponding channel of the detector; and the detector comprising a plurality of detection channels, the detector configured to output optical coherence tomography data indicative of a structure of the sample at a plurality of locations that generated the plurality of backscattered light samples.

In some embodiments, the light source is a wavelength-swept laser.

In some embodiments, the wavelength-swept laser is configured to operate at a 125 kilohertz A-scan rate.

In some embodiments, the light source is a wavelength-stepped frequency comb source.

In some embodiments, the sample arm further comprises: a first spatial separator mechanically coupled to a distal end of each optical fiber of the first plurality of optical fibers.

In some embodiments, the first spatial separator comprises a V-groove assembly.

In some embodiments, the reference arm further comprises: a second spatial separator mechanically coupled to a distal end of each optical fiber of the second plurality of optical fibers.

In some embodiments, the particular spectral range is centered at 1300 nanometers.

In some embodiments, the first splitter comprises a planar lightwave circuit splitter that receives light from the first optical fiber and splits the received light into n outputs.

In some embodiments, the first spatial separator comprises a V-groove assembly.

In some embodiments, the first plurality of optical components comprises: a first lens having a first side optically coupled to the first plurality of optical fibers and a second side, wherein the first lens is configured to focus the plurality of beams at a first focal distance corresponding to a focal length of the first lens; a surface configured to redirect light received from the second side of the first lens toward a first side of a second lens and redirect light received from the first side of the second lens toward the second side of the first lens; the second lens having the first side optically coupled to the surface and a second side configured to direct light received from the surface toward the sample and receive the plurality of backscattered light samples from the sample.

In some embodiments, the first plurality of optical components comprises: a third lens having a first side optically coupled to the first plurality of optical fibers and a second side, wherein the third lens is configured to focus the plurality of beams at a first focal distance corresponding to a focal length of the third lens; a polarizing beam splitter comprising a first port, a second port, and a third port and a first interface that passes light having a first polarization and redirects light having a second polarization, wherein the beam splitter is configured to pass light having the first polarization received at the first port to the second port and redirect light having the second polarization received at the second port toward the third port, wherein the first port is optically coupled to the second side of the third lens such that the first port receives the plurality of beams from the third lens, wherein the second port is optically coupled to a first side of a fourth lens such that the second port emits the plurality of beams toward the fourth lens and receives the plurality of backscattered samples from the fourth lens, and wherein the third port is configured to emit the plurality of samples toward a fifth lens; the fourth lens having the first side optically coupled to the second port and having a second side; a quarter wave plate optically coupled to the second side of the fourth lens and a first side of the first lens, wherein the first side of the first lens is optically coupled to the quarter wave plate; and the fifth lens having a first side optically coupled to the third port of the polarizing beam splitter and a second side optically coupled to a third plurality of optical fibers, wherein the first plurality of optical fibers and the third plurality of optical fibers are oriented such that light emitted from the first plurality of optical fibers is transmitted to respective optical fibers of the third plurality of optical fibers.

In some embodiments, the first plurality of optical components comprises: a plurality of optical circulators, each of the optical circulators having a first port, a second port, and a third port, wherein the first port of each of the plurality of optical circulators is optically coupled to the light source via a respective optical fiber of the first plurality of optical fibers, the second port of each of the plurality of optical circulators is optically coupled to the sample via a respective optical fiber of a third plurality of optical fibers, and the third port of each of the plurality of optical circulators is optically coupled to the second plurality of optical components via a respective optical fiber of a fourth plurality of optical fibers.

In some embodiments, the system further comprises a spatial separator mechanically coupled to a distal end of each optical fiber of the third plurality of optical fibers, and disposed to optically couple each optical fiber of the third plurality of optical fibers to the first side of the first lens.

In some embodiments, the first plurality of optical components comprises: a second planar lightwave circuit comprising a plurality of optical couplers, each having a first port, a second port, and a third port, wherein the first port of each of the plurality of optical couplers is optically coupled to the light source via a respective optical fiber of the first plurality of optical fibers, the second port of each of the plurality of optical couplers is optically coupled to the sample via a respective optical fiber of a third plurality of optical fibers, and the third port of each of the plurality of optical couplers is optically coupled to the second plurality of optical components via a respective optical fiber of a fourth plurality of optical fibers.

In some embodiments, each of the plurality of optical couplers is configured to: output, from the third port, a first fraction of light received at the first port; output, from a fourth port, a second fraction of light received at the first port; output, from the first port, the first fraction of light received at the third port; and output, from the second port, the second fraction of light received at the third port.

In some embodiments, a ratio between the first fraction and the second fraction is approximately equal to one.

In some embodiments, a ratio between the first fraction and the second fraction is less than one.

In some embodiments, the system further comprises a spatial separator mechanically coupled to a distal end of each optical fiber of the third plurality of optical fibers, and disposed to optically couple each optical fiber of the third plurality of optical fibers to the first side of the first lens.

In some embodiments, the second plurality of optical components comprises a beam splitter comprising a first port, a second port, and a third port, wherein the first port is configured to receive light emitted by the second plurality of optical, wherein the second port is configured to receive the plurality of backscattered light samples, and wherein the third port is configured to output the plurality of fringes.

In some embodiments, the detector comprises a plurality of balanced detectors comprising a first port and a second port, each of the plurality of balanced detectors corresponding to a respective channel of the detector, wherein the beam splitter further comprises a fourth port configured to output a second plurality of fringes, and wherein each of the plurality of balanced detectors receives a fringe of the plurality of fringes and a corresponding fringe of the second plurality of fringes, and outputs a signal based on both fringes.

In some embodiments, the second plurality of optical components comprises: a plurality of optical couplers, each having a first port, a second port, a third port, and a fourth port, wherein the first port is coupled to the light source via a respective optical fiber of the second plurality of optical fibers; the second port is coupled to the sample via a respective optical fiber of a plurality fourth plurality of optical fibers; the third port is coupled to a respective channel of the plurality of detection channels; and the fourth port is coupled to the respective channel of the plurality of detection channels.

In some embodiments, each of the plurality of optical couplers is a discrete fiber coupler.

In some embodiments, the system further comprises a third planar lightwave circuit, wherein the planar lightwave circuit comprises the plurality of optical couplers.

In some embodiments, the reference arm further comprises a modulation component disposed between the light source and the second splitter, the modulation component configured to modulate at least polarization of light provided to the second splitter.

In some embodiments, the reference arm further comprises a modulation component disposed between the light source and the second splitter, the modulation component configured to modulate at least a phase of light provided to the second splitter.

In some embodiments, the reference arm further comprises a modulation component disposed between the light source and the second splitter, the modulation component configured to: modulate a phase of light provided to the second splitter; and modulate polarization of light provided to the second splitter.

In some embodiments, the sample arm further comprises a modulation component disposed between the light source and the first splitter, the modulation component configured to modulate at least polarization of light provided to the first splitter.

In some embodiments, the sample arm further comprises a modulation component disposed between the light source and the first splitter, the modulation component configured to modulate at least a phase of light provided to the first splitter.

In some embodiments, the sample arm further comprises a modulation component disposed between the light source and the first splitter, the modulation component configured to: modulate a phase of light provided to the first splitter; and modulate polarization of light provided to the first splitter.

In some embodiments, the modulation component comprises: a coupler comprising: a first port optically coupled to the light source; a second port; and a third port; a first phase modulator comprising: a first port optically coupled to the second port of the coupler; and a second port; a second phase modulator comprising: a first port optically coupled to the third port of the coupler; and a second port; and a beam combiner comprising: a first port optically coupled to the first phase modulator; a second port optically coupled to the second phase modulator; and a third port.

In some embodiments, the modulation component further comprises: a polarization controller optically coupled to the second port of the coupler and the first port of the first phase modulator.

In some embodiments, the modulation component further comprises: a polarization controller optically coupled to the third port of the coupler and the sport of the second phase modulator.

In some embodiments, a system for multiple beam optical coherence tomography, comprising: a first splitter arranged to receive first light from a light source and output a fraction of the first light to each of a first plurality of waveguides; optical components arranged to: receive light from the first plurality of waveguides; direct the received light as a plurality of beams toward a sample such that each of the plurality of beams impinges the sample at a different lateral position; and collect a plurality of backscattered light samples from the different lateral positions of the sample; a second splitter arranged to receive second light from the light source and output a fraction of the second light to each of a second plurality of waveguides as a plurality of reference light samples; a mixer arranged to receive the plurality of backscattered light samples and the plurality of reference light samples and combine each backscattered light sample with a corresponding reference light sample such that the mixer outputs a plurality of fringes; and a detector arranged to receive the plurality of fringes and output a plurality of optical coherence tomography signals, wherein each of the plurality of optical coherence tomography signals is indicative of a structure of the sample at a respective lateral position.

In some embodiments, the plurality of beams comprises eight beams.

In some embodiments, the first splitter comprises a planar lightwave circuit splitter.

In some embodiments, wherein the optical components comprise: a plurality of optical circulators, each of the plurality of optical circulators arranged to: receive a beam of the plurality of beams from a waveguide of the first plurality of waveguides; direct the received beam toward the sample; and direct a backscattered light sample toward the detector.

In some embodiments, the optical components comprise: a plurality of optical couplers, each of the plurality of optical circulators arranged to: receive a beam of the plurality of beams from a waveguide of the first plurality of waveguides; direct the received beam toward the sample; and direct a backscattered light sample toward the detector.

In some embodiments, the system comprises the light source.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 6A shows an example of an arrangement of components that can be used to align multiple optical fibers across a free space gap in accordance with some embodiments of the disclosed subject matter.

FIG. 6B shows a side view of the arrangement of components shown in FIG. 6A in accordance with some embodiments of the disclosed subject matter.

DETAILED DESCRIPTION

In accordance with some embodiments of the disclosed subject matter, mechanisms (which can include systems, methods, and media) for multiple beam optical coherence tomography are provided.

In accordance with some embodiments, the mechanisms described herein can use an optical light source which determines a single channel imaging speed, a single waveguide-based reference arm and a single waveguide-based sample arm, each including a first optical subsystem that can be used to generate a set of multiple electromagnetic radiations. In some embodiments, the sample arm can include a second optical subsystem that can be used to probe a set of sample locations using the multiple radiations provided by the first optical subsystem in the sample arm, and collect corresponding backscattered radiations from the sample. In some embodiments, a third optical subsystem can receive reference electromagnetic radiations from the reference arm, and can combine the reference electromagnetic radiations with corresponding backscattered radiations to generate a set of interference fringes. In some embodiments, a detection and processing arrangement can separately record the interference fringes in each imaging channel, and the recorded information from the interference fringes can be used to generate multiple OCT signals representing different portions of the sample.

Figure 1:
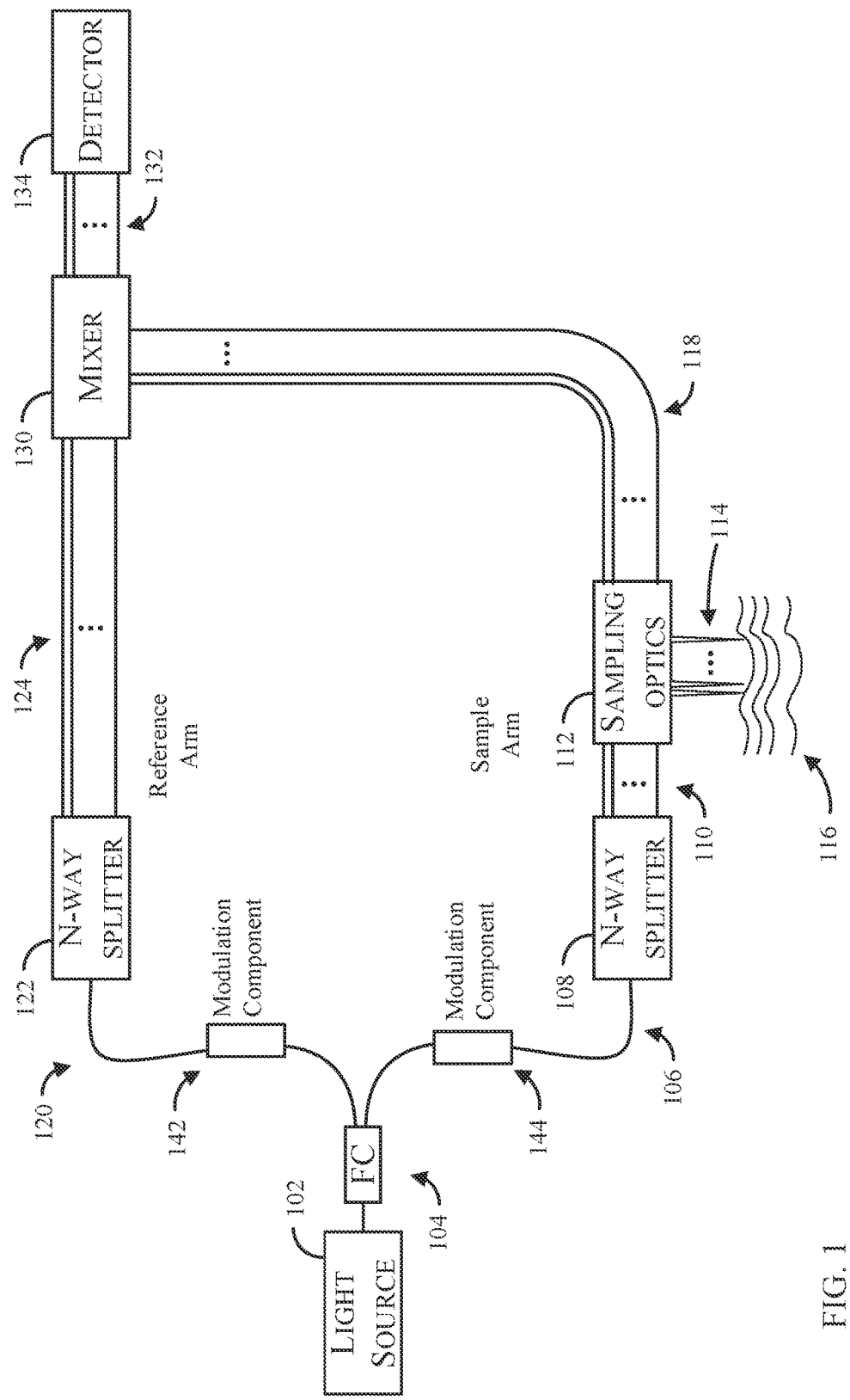
FIG. 1 shows an example of a system for multiple beam optical coherence tomography in accordance with some embodiments of the disclosed subject matter.

FIG. 1 shows an example 100 of a system for multiple beam optical coherence tomography in accordance with some embodiments of the disclosed subject matter. In some embodiments, system 100 can include a light source 102 that is suitable for generating OCT signals. For example, light source 102 can be a wavelength-swept laser. In such an example, the wavelength-swept laser can be operated at any suitable A-scan rate (e.g., the number of times the entire wavelength range is swept per time-period), and can be centered at any suitable frequency. In a more particular example, the A-scan rate can be about 125 kilohertz (kHz) with a center wavelength at 1300 nanometers (nm). As another example, light source 102 can be a frequency comb source such as a wavelength-stepped frequency comb source. In such an example, the wavelength-stepped frequency comb source can be operated at any suitable A-scan rate (e.g., the number of times the entire wavelength range is stepped through per time-period), and can be centered at any suitable frequency. For example, the A-scan rate can be about 125 kHz, 250 kHz, 500 kHz, 1 MHz, 2 MHz, 4 MHz or any other suitable rate, with a center wavelength at about 1300 nanometers (nm), 1050 nm, 1580 nm, or any other suitable wavelength. In further specific examples, light source 102 can be implemented using a Fourier-domain mode-locked laser, a vertical cavity surface emitting laser, a stretched pulse mode-locked laser, and a phase-code mode-locked laser.

In some embodiments, light source 102 can be coupled to a sample arm and a reference arm of system 100 using any suitable optical component or components. For example, a fiber coupler 104 can receive light from light source 102 (e.g., via an electromagnetic waveguide, such as an optical fiber, optically coupled between an output of light source 102 and an input port of fiber coupler 104), and can output a first portion of light toward the sample arm and a second portion of the light toward the reference arm. In some embodiments, any suitable portion of the source light can be directed toward the sample arm. For example, more than half of source light received at fiber coupler 104 can be directed toward the sample arm and less than half can be directed toward the reference arm. As a more particular example, about 80% of source light received at fiber coupler 104 can be directed toward the sample arm and 20% can be directed toward the reference arm.

In some embodiments, the sampling arm can include an electromagnetic waveguide, such as a single mode optical fiber 106, that is optically coupled to an output of fiber coupler 104 and an input of an N-way optical splitter 108. In some embodiments, N-way splitter 108 can be implemented using any suitable optical component or combination of components. For example, N-way splitter 108 can be implemented as an N-way planar lightwave circuit. As another example, N-way splitter 108 can be implemented as a fused optical fiber splitter that is monolithically constructed. As yet another example, N-way splitter 108 can be implemented as a fused optical fiber splitter that is formed by cascading optical splitters.

In some embodiments, outputs of N-way splitter 108 can be coupled to N electromagnetic waveguides, such as a fiber bundle 110. In some embodiments, fiber bundle 110 can be implemented using any suitable component or combination of components. For example, an optical fiber ribbon including at least N optical fibers can be used to implement fiber bundle 110. In some embodiments, each optical fiber in fiber bundle 110 can be a single mode optical fiber.

In some embodiments, an output of each of optical fiber of N optical fibers 110 can be coupled to sampling optics 112. In some embodiments, sampling optics can receive light from each optical fiber of fiber bundle 110, convert the light from each fiber into a beam of light, and focus the resulting N beams 114 at or near a surface of a sample 116.

Sample 116 can backscatter and return a portion of each beam to sampling optics 112. Sampling optics 112 can receive the backscattered light from sample 116, and direct the backscattered light from each of N beams 114 onto N electromagnetic waveguides, such as respective fibers of fiber bundle 118. In some embodiments, fiber bundle 118 can be implemented using components similar to the components used to implement fiber bundle 110. In some embodiments, each optical fiber in fiber bundle 118 can be a single mode optical fiber.

In some embodiments, the reference arm can include an electromagnetic waveguide, such as a single mode optical fiber 120, that is optically coupled to an output of fiber coupler 104 and an input of an N-way optical splitter 122. In some embodiments, N-way splitter 122 can be implemented using any suitable optical component of combination of components. For example, N-way splitter 122 can be implemented using components similar to the components used to implement N-way splitter 108.

In some embodiments, outputs of N-way splitter 122 can be coupled to N electromagnetic waveguides, such as individual fibers of a fiber bundle 124. In some embodiments, fiber bundle 124 can be implemented using any suitable component or combination of components. For example, fiber bundle 124 can be implemented using components similar to the components used to implement fiber bundle 110. In some embodiments, each optical fiber in fiber bundle 124 can be a single mode optical fiber.

In some embodiments, a distal end of fiber bundle 118 can be optically coupled to a first set of inputs to a mixer 130, and a distal end of fiber bundle 124 can be optically coupled to a second set of inputs to mixer 130. In some embodiments, mixer 130 can convert the light from each individual fiber of fiber bundle 118 and fiber bundle 124 into a beam, and combine each beam from fiber bundle 118 with a corresponding beam from fiber bundle 124.

In some embodiments, differences between the path lengths of the beam from the sample arm (e.g., in the backscattered light from the sample) and the reference arm can cause an interference pattern that is related to the structure of sample 116 when the signals are combined. In some embodiments, the optical path length of the reference arm and the sample arm can be approximately equal. Additionally, in some embodiments, a path length of the reference arm and/or sample arm can be variable to adjust the target distance of OCT system 100.

In some embodiments, outputs of mixer 130 can be coupled to N electromagnetic waveguides, such as a fiber bundle 132. In some embodiments, fiber bundle 132 can be implemented using any suitable component or combination of components. For example, an optical fiber ribbon including at least N optical fibers can be used to implement fiber bundle 132. Additionally, in some embodiments, mixer 130 can be coupled to 2N electromagnetic waveguides (e.g., two fiber bundles 132) in which pairs of electromagnetic waveguides convey related signals.

In some embodiments, a detector 134 can be coupled to an output or outputs of mixer 130, and can generate OCT signals for each of the N beams that were incident on sample 116. In some embodiments, detector 134 can be implemented using any suitable technique or combination of techniques. For example, as described below in connection with FIG. 5, detector 134 can be implemented using balanced detectors that each receive a pair of fringe signals from mixer 130, and each provide an output to a corresponding channel of a data acquisition board. In some embodiments, signals from detector 134 can be used to generate OCT images depicting structure of sample 116.

In some embodiments, the reference arm can include a component 142 (sometimes referred to herein as a phase controller, a polarization controller, and/or a modulation component), that can be configured to induce a common optical function that affects beams that propagate via the reference arm (e.g., all N beams that propagate via fiber bundle 124). For example, in some embodiments, modulation component 142 can be configured to modulate a phase of electromagnetic radiation in the reference arm, to modulate polarization of electromagnetic radiation in the reference arm, to modulate a phase and polarization of electromagnetic radiation in the reference arm, to modulate or shift the optical frequency of the electromagnetic radiation in the reference arm, and/or to perform any other suitable functions. In a more particular example, modulation component 142 can be implemented as an optical phase modulator. In another particular example, modulation component 142 can be implemented as an optical polarization modulator. In yet another more particular example, modulation component 142 can be implemented as an optical phase and polarization modulator.

In some embodiments, modulation of a phase of electromagnetic radiation (e.g., by modulation component 142) can generate complex fringe signals (e.g., a signal with components that can be detected using heterodyne detection techniques). For example, modulating a phase of electromagnetic radiation in the reference arm can cause complex fringe signals to be generated when the phase-modulated electromagnetic radiation in the reference arm interacts with electromagnetic radiation in the sample arm (e.g., within mixer 130). Information encoded within complex fringe signals can be used to discriminate between positive and negative optical delay spaces in OCT and subsampled OCT (sometimes referred to as circular-ranging OCT).

In some embodiments, modulation component 142 can be configured as a phase modulator using any suitable technique or combination of techniques. For example, modulation component 142 can be, and/or include, an electro-optic modulator. In a more particular example, modulation component 142 can be a lithium niobate modulator. As another example, modulation component 142 can be, and/or include, an acousto-optic modulator. In a more particular example, modulation component 142 can be an optical frequency shifter.

In some embodiments, modulating polarization of electromagnetic radiation (e.g., by modulation component 142) can facilitate polarization-diverse interferometric measurements. For example, interference between electromagnetic radiation propagated on the reference arm and electromagnetic radiation propagated on the sample arm can be measured separately in two or more distinct polarization states. Polarization-diverse interferometric measurement can increase a signal-to-noise ratio in detected signals.

In some embodiments, modulation component 142 can be configured as a polarization modulator using any suitable technique or combination of techniques. For example, modulation component 142 can be, and/or include, an electro-optic or acousto-optic modulator that induces a different phase modulation in transverse electric (TE) and transverse magnetic (TM) optical modes, resulting in a modulation of the optical polarization. As a more particular example, a lithium niobate modulator can be used to provide an electro-optic modulator with different phase responses in TE and TM optical modes.

In some embodiments, the sample arm can include a component 144 (sometimes referred to herein as a phase controller, a polarization controller, and/or a modulation component), that can be configured to induce a common optical function that affects beams that propagate via the sample arm (e.g., all N beams that propagate via fiber bundle 110). In some embodiments, modulation component 144 can be configured to modulate a phase, polarization, and/or optical frequency of electromagnetic radiation in the sample arm using any suitable techniques, such as techniques described above in connection with modulation component 142.

In some embodiments, modulation component 142 and/or modulation component 144 can be omitted. Additionally or alternatively, in some embodiments, modulation component 142 can include a phase modulator, and modulation component 144 can omit a phase modulator (or vice versa). In some embodiments, modulation component 142 and modulation component 144 can include polarization modulators.

In some embodiments, modulation component 142 and/or modulation component 144 can be configured to induce a phase and/or polarization modulation that induces modulations between subsequent A-lines, or it can induce modulations within an A-line. Additionally, when light source 102 is implemented as a wavelength-stepped frequency comb, modulation component 142 and/or modulation component 144 can induce modulation between subsequent A-lines, between the optical pulses of the wavelength-stepped frequency comb source, etc.

In some embodiments, the reference arm can include a variable optical delay element (not shown) to control optical delay of the electro-magnetic radiation in each of the reference arm fibers (e.g., fibers of fiber bundle 124). For example, the optical delay component can be located before splitter 122 (e.g., in connection with fiber 120), such that the optical delay affects all beams in the reference arm. The variable optical delay can be implemented using any suitable technique or combination of techniques. For example, the variable optical delay can be implemented using a mirror on a translation stage along with an optical circulator disposed between portions of fiber 120 (e.g., light from fiber coupler 104 and/or modulation component 142 can be directed toward the mirror by the optical circulator, and light reflected by the mirror can be directed toward splitter 122 by the optical circulator). As another example, a free-space coupling arrangement can be disposed between portions of fiber 120, and a distance between the portions of fiber 120 can be varied (e.g., using a translation stage). Additionally or alternatively, a variable optical delay element can be located in the sample arm (e.g., in connection with fiber 106).

Figure 2:
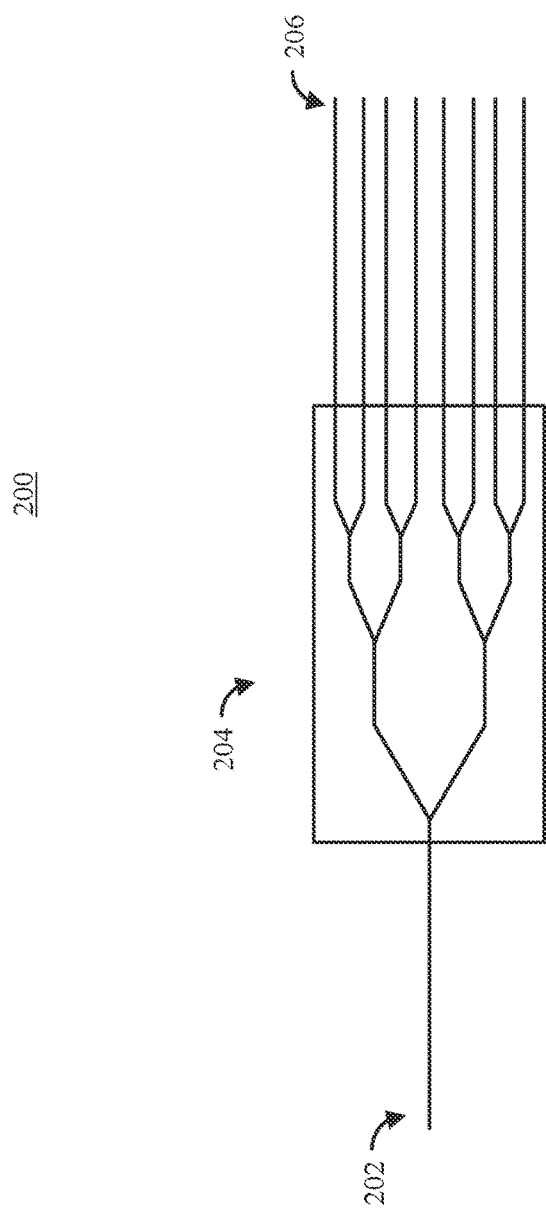
FIG. 2 shows an example of a splitter that can be used to implement a portion of system for multiple beam optical coherence tomography in accordance with some embodiments of the disclosed subject matter.

FIG. 2 shows an example 200 of a splitter that can be used to implement a portion of system 100 for multiple beam optical coherence tomography in accordance with some embodiments of the disclosed subject matter. In some embodiments, splitter 200 can have an input coupled to and/or implemented by an electromagnetic waveguide. For example, an optical fiber 202 can serve as and/or be coupled to an input of splitter 200.

In some embodiments, a proximal end of optical fiber 202 can be coupled to a light source (e.g., light source 102), and a distal end of optical fiber 202 can be coupled to splitting optics 204. For example, optical fiber 202 can be used to implement at least a portion of optical fiber 106 or optical fiber 120.

In some embodiments, splitting optics 204 can be implemented using any suitable technique or combination of techniques. For example, splitting optics 204 can be implemented using a planar lightwave circuit. As another example, as described above in connection with N-way splitter 108, splitting optics 204 can be implemented as a fused optical fiber splitter. In some embodiments, splitting optics 204 can divide light received via optical fiber 202 into any suitable number of parts. For example, in some embodiments, splitting optics 204 can be a 1×8 planar lightwave circuit that divides into light into eight substantially equal parts. As another example, splitting optics 204 can be implemented by cascading and/or otherwise combining smaller planar lightwave circuits, such as multiple 1×2 planar lightwave circuit splitters.

In some embodiments, outputs of splitting optics 204 can be coupled to a group of optical fibers 206 each having a proximal end optically coupled to a channel of splitting optics 204 and a distal end that can be coupled to another optical device. For example, optical fibers 206 can be used to implement at least a portion of fiber bundle 110 or fiber bundle 124.

Figure 3:
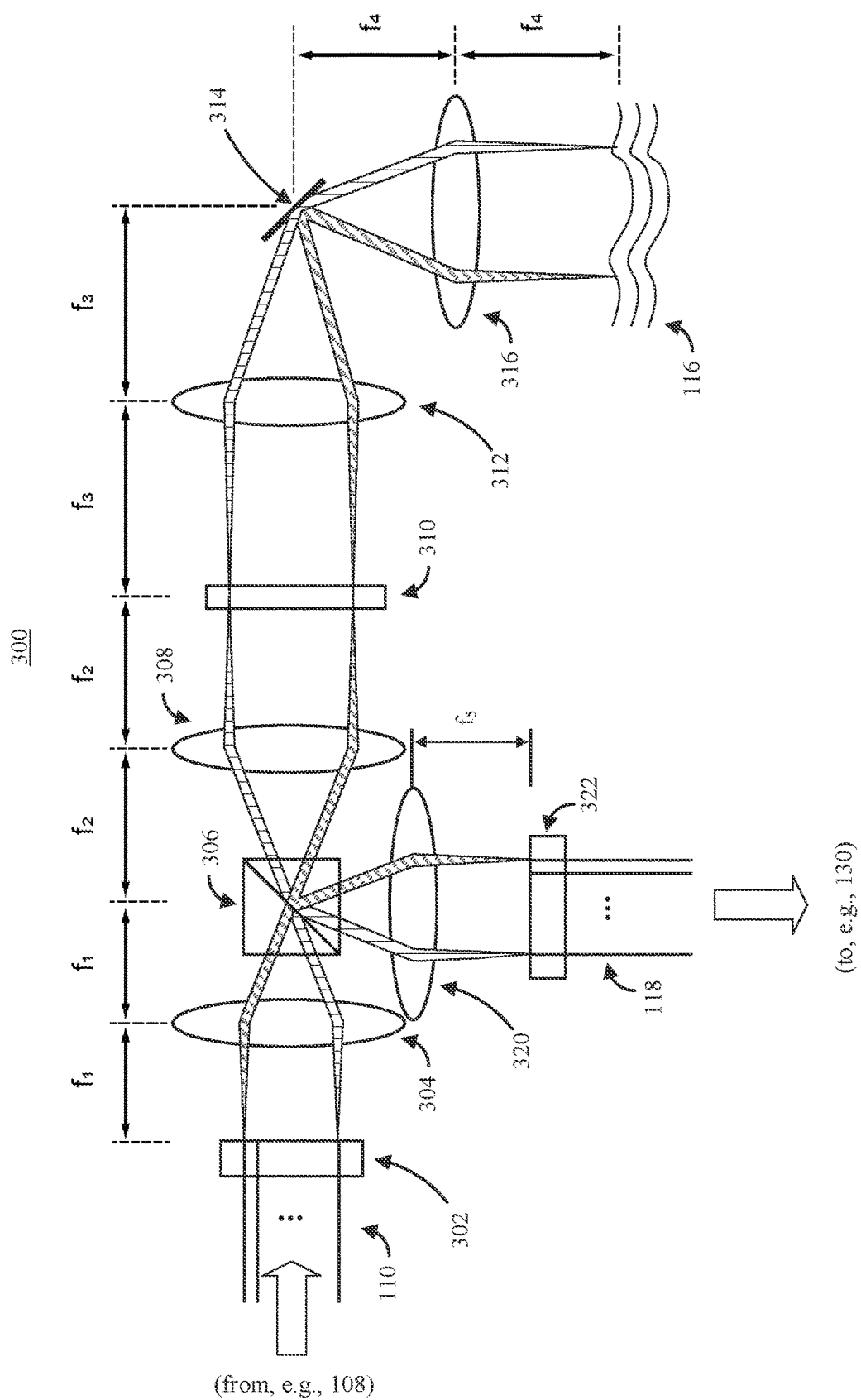
FIG. 3 shows an example of sampling optics that can be used to implement a portion of the system shown in FIG. 1 for multiple beam optical coherence tomography in accordance with some embodiments of the disclosed subject matter.

FIG. 3 shows an example 300 of sampling optics that can be used to implement a portion of system 100 for multiple beam optical coherence tomography in accordance with some embodiments of the disclosed subject matter. As shown in FIG. 3, sampling optics 300 can receive multiple portions of light from a light source (e.g., via N-way splitter 108). In some embodiments, sampling optics 300 can include a spatial separator 302 that is configured to mechanically position the distal end of various optical fibers in an optical fiber bundle (e.g., optical fiber bundle 110) such that a face of each optical fiber is held at a particular position and orientation relative to other optical components of sampling optics 300. For example, the core of each individual optical fiber of optical fiber bundle 110 can be positioned by placing the cladding surrounding the core into a v-shaped groove that is sized to precisely position an individual optical fiber including a core and cladding. Spatial separator 302 can position fibers at specific locations defined in 1 dimension (e.g., using a linear V-groove) or 2 dimensions (e.g., as an array). In some embodiments, spatial separator 302 can be implemented using any suitable components. For example, spatial separator 302 can be implemented as a V-groove assembly, such as a single-mode V-groove assembly available from OZ Optics headquartered in Ottawa, Canada. As another example, spatial separator 302 can be implemented as an array of wells or through-holes in a material (e.g., glass, silicon-dioxide, etc.) into which individual fibers in a set of fibers can be fixed such that the face of each fiber is precisely aligned with respect to each other fiber. In such an example, such wells or through-holes can be generated mechanically (e.g., using mechanical drilling tools) and/or using other processes (e.g., photolithography). In such an example, the wells or through-holes of the array can be arranged in any suitable one dimensional or two dimensional layout (e.g., as a single row or column, as a set of rows or columns, as a series of concentric circles, etc.) As yet another example, spatial separator 302 can be implemented as one or more multi-core fibers in which each optical core is arranged at a specific locations relative to each other optical core within the multi-core fiber.

In some embodiments, a first lens 304 can be optically coupled to the optical fibers of fiber bundle 110. As shown in FIG. 3, first lens 304 can be arranged such that the face of each optical fiber of fiber bundle 110 coincides with the focal length $f_1$ of first lens 304, and emits a beam from a point that is a particular radial distance from the optical axis of first lens 304. As shown in FIG. 3, first lens 304 can be implemented as biconvex lens. However, this is merely an example, and many types of lens can be used to implement first lens 304 (and other lenses shown in the drawings as biconvex lenses). For example, without excluding any suitable types of lenses, other types of lenses that can be used to implement mechanisms described herein for multiple beam optical coherence tomography (e.g., lenses shown in FIGS. 3, 4, 6A, 6B, and 11) include plano-convex lenses, achromatic doublet lenses, Fresnel lenses, and gradient-index (GRIN) lens. In some embodiments, if spatial separator 302 is used to arrange the optical fibers of fiber bundle 110 in a straight line, such that the beams emitted by the optical fibers are all co-planar, spatial separator 302 can be positioned with respect to first lens 304 such that the optical axis of first lens 304 is on the same plane as the beams. For example, this arrangement can facilitate alignment of one or more other components with spatial separator 302 and first lens 304.

In some embodiments, optical fibers of fiber bundle 110 can emit an individual beam toward a first side of first lens 304, which can focus the light received from optical bundle 110 at focal length $f_1$ on a distal side of first lens 304. This can cause the beams from each of the various optical fibers to converge at the focal point of first lens 304. In the absence of other optical components, these beams would diverge again after the focal point such that at a distance $2*f_1$ from the face of the optical fibers the beams are mirrored across the optical axis and can be collected by an array of optical fibers having mirror image positions to the optical fibers positioned by spatial separator 302.

In some embodiments, sampling optics 300 can include a polarizing beam splitter 306 arranged at a focal point of first lens 304 and/or a second lens 308. In some embodiments, polarizing beam splitter 306 can receive light from first lens 304, and can emit substantially all of the light that has a first linear polarization toward second lens 308, and can deflect any light having a second orthogonal polarization toward a second optical axis. In some embodiments, the sample arm can include a polarization controller (not shown) to cause the light emitted from fiber bundle 110 to be uniformly polarized such that substantially all of the light emitted from fiber bundle 110 is transmitted by polarizing beam splitter 306 toward second lens 308.

In some embodiments, beams emitted by first lens 304 can converge at the interface of polarizing beam splitter 306, and can begin to diverge as the beams travel toward a first side of second lens 308. Second lens 308 can be arranged such that the interface of polarizing beam splitter 306 coincides with a focal length $f_2$ of second lens 308. In some embodiments, the focal length of first lens 304 and second lens 308 can be the same (e.g., such that $f_1=f_2$), but this is merely an example and the focal length of the lenses can differ.

In some embodiments, second lens 308 can focus the diverging beams such that the beams form substantially parallel beams traveling parallel to the optical axis of second lens 308. As shown in FIG. 3, in some embodiments, second lens 308 can cause each beam to converge to a point at the focal length $f_2$. For example, when the interface of polarizing beam splitter 306 is placed at a distance equal to the focal length $f_2$ from the first side of second lens 308, each beam can converge at a distance equal to the focal length $f_2$ on the second side of second lens 308.

In some embodiments, sampling optics 300 can include a quarter wave plate 310 arranged at the focal plane of second lens 308 and a focal plane of a third lens 312. In some embodiments, quarter wave plate 310 can be arranged to shift the polarization of light received from second lens 308 to a circular polarization. For example, in some embodiments, quarter wave plate 310 can be arranged such that the fast axis of quarter wave plate 310 at a 45° angle with respect to the input polarization axis, which can cause the output light to be circularly polarized. In some embodiments, each beam can be emitted from quarter wave plate 310 toward a first side of third lens 312. Third lens 312 can be arranged such that the center of quarter wave plate 310 coincides with a focal length $f_3$ of third lens 312. In some embodiments, the focal length of third lens 312 can be the same or different than the focal length of first lens 304 and/or second lens 308. In some embodiments, third lens 312 can focus the light received from quarter wave plate 310 at focal length $f_3$ on a distal side of third lens 312. This can cause the beams corresponding to each of the various optical fibers in fiber bundle 110 to converge at the focal point of third lens 312.

In some embodiments, sampling optics 300 can include a reflector 314 that redirects light received from third lens 312 toward sample 116. Reflector 314 can be arranged such that a reflecting surface of reflector 314 coincides with the focal length $f_3$ of third lens 312. In some embodiments, reflector 314 can be implemented using any suitable reflective surface, such as a planar mirror, a galvanometer, a micro-electro-mechanical system (MEMS)-based mirror, a polygon mirror scanner, etc. In some embodiments, an angle of reflector 314 can be fixed or adjustable. For example, in some embodiments, reflector 314 can be a surface of a galvo scanner that can be used to control an angle that reflector 314 makes with an optical axis of third lens 312.

In some embodiments, beams emitted by third lens 312 can converge at the reflective surface of reflector 314, and can begin to diverge as the beams travel toward a first side of a fourth lens 316. Fourth lens 316 can be arranged such that the reflective surface of reflector 314 coincides with a focal length $f_4$ of fourth lens 316. In some embodiments, the focal length of fourth lens 316 can be the same or different than the focal length of first lens 304, second lens 308, and/or third lens 312.

In some embodiments, fourth lens 316 can focus the diverging beams such that the beams form substantially parallel beams traveling parallel to the optical axis of fourth lens 316 when the beams intersect a surface of sample 116. As shown in FIG. 3, in some embodiments, fourth lens 316 can cause each beam to converge to a point at the focal length $f_4$. For example, when the reflective surface of reflector 314 is placed at a distance equal to the focal length $f_4$ from the first side of fourth lens 316, each beam can converge at a distance equal to the focal length $f_4$ on the second side of fourth lens 316, and can begin diverging past the distance equal to the focal length $f_4$ (e.g., forming a beam waist at the focal length $f_4$).

In some embodiments, sample 116 can backscatter one or more portions of the light incident on the sample from each beam. The depth at which the light is backscattered can depend on the structure of sample 116 and/or the wavelength of the incident light. This can cause different amounts of phase shift between the backscattered light and light that traversed the reference arm. Additionally, light backscattered by sample 116 can have its polarization inverted.

In some embodiments, the light backscattered by sample 116 can traverse the same path through sampling optics 300 as the incident light from light source 102 in reverse, with the polarization being adjusted by quarter wave plate to be a linear polarization with an offset of 90 degrees from the incident light such that a substantial portion of the backscattered light is redirected by polarizing beam splitter 306 on a path coinciding with the second optical axis of polarizing beam splitter 306 (e.g., an optical path that is substantially orthogonal to the optical axis of first lens 304 and second lens 308).

In some embodiments, beams of backscattered light emitted from the proximal side of second lens 308 can converge at the interface of polarizing beam splitter 306 which can reflect the backscattered light. The beams of backscattered light can then begin to diverge as the beams travel toward along the second optical axis of polarizing beam splitter 306 toward a first side of a fifth lens 320. Fifth lens 320 can be arranged such that the interface of polarizing beam splitter 306 coincides with a focal length $f_5$ of fifth lens 320. In some embodiments, the focal length of fifth lens 320 can be the same or different than the focal length of first lens 304, second lens 308, third lens 312, and/or fourth lens 316. For example, to maintain consistent beam spacing on the first side of first lens 304 and the second side of fifth lens 320 (e.g., such that the spacing of spatial separator 302 and a second spatial separator, described below, can be made consistent), the focal length of first lens 304 and fifth lens 320 can be configured to have the same focal length (e.g., such that $f_1=f_5$).

In some embodiments, sampling optics 300 can include a second spatial separator 322 that is configured to mechanically position the proximal end of various optical fibers in an optical fiber bundle (e.g., optical fiber bundle 118) such that a face of each optical fiber is held at a particular position and orientation relative to other optical components of sampling optics 300. For example, the core of each individual optical fiber of optical fiber bundle 118 can be positioned by placing the cladding surrounding the core into a v-shaped groove that is sized to precisely position an individual optical fiber including a core and cladding. In some embodiments, spatial separator 322 can be implemented using any suitable components, such as components described above in connection with spatial separator 302. In some embodiments, second spatial separator 322 can be positioned such that the beams of backscattered light emitted from the second side of fifth lens 320 are each received by a corresponding optical fiber. As described below, an alignment system can be used to precisely align spatial separator 322 such that the beams of backscattered light are received at corresponding optical fibers, which can convey the backscattered light to a mixer (e.g., mixer 130).

Figure 4:
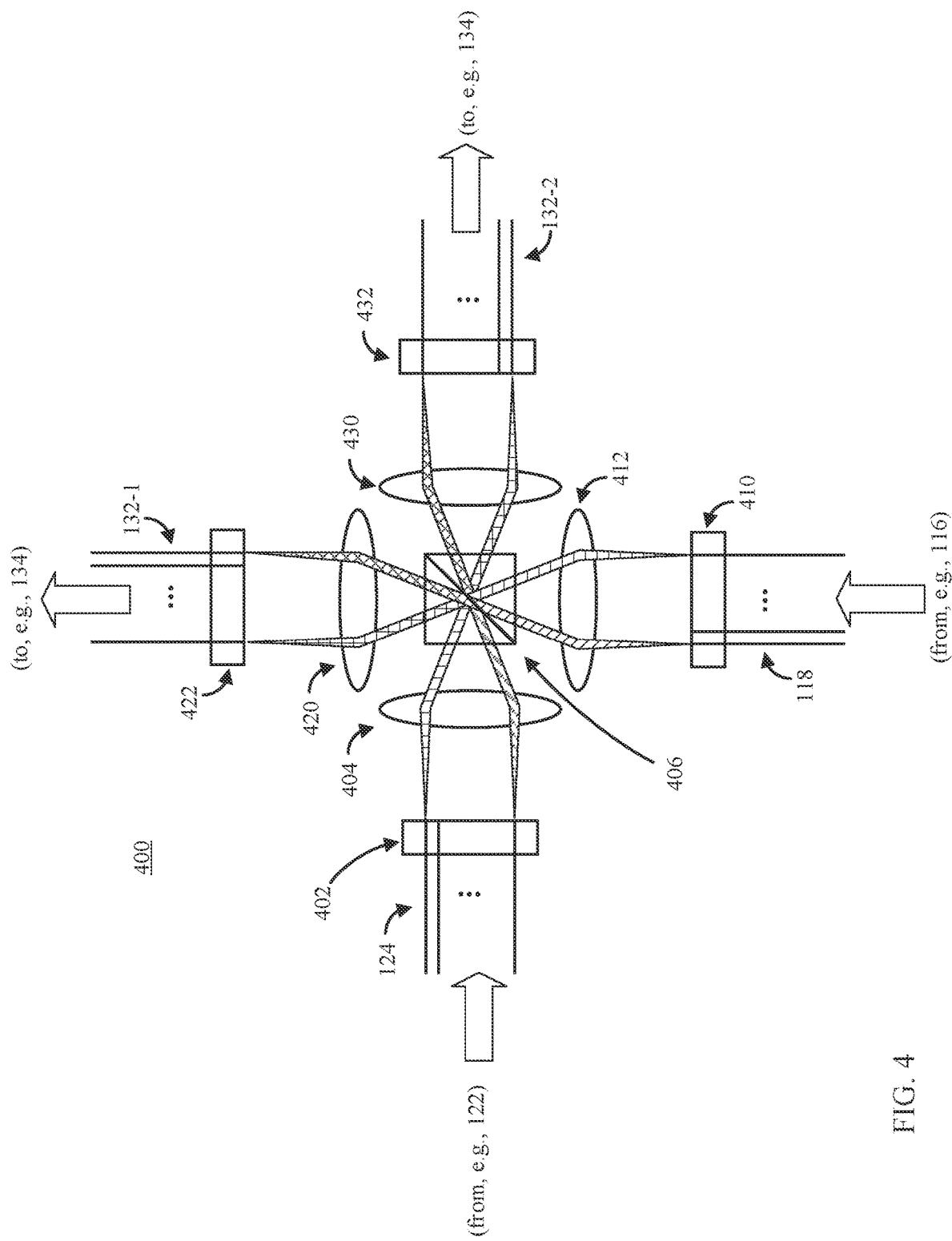
FIG. 4 shows an example of optics that can be used to implement a mixing portion of a multi-beam interferometer for multiple beam optical coherence tomography in accordance with some embodiments of the disclosed subject matter.

FIG. 4 shows an example 400 of optics that can be used to implement a mixing portion of a multi-beam interferometer for multiple beam optical coherence tomography in accordance with some embodiments of the disclosed subject matter. As shown in FIG. 4, free space mixer 400 can be implemented using various optical components. In some embodiments, free space mixer 400 can include a spatial separator 402 that is configured to mechanically position the distal end of various optical fibers in an optical fiber bundle (e.g., optical fiber bundle 124) such that a face of each optical fiber is held at a particular position and orientation relative to other optical components of free space mixer 400. In some embodiments, spatial separator 402 can be implemented using any suitable components, such as components described above in connection with spatial separator 302 of FIG. 3.

In some embodiments, a first lens 404 can be optically coupled to the optical fibers of fiber bundle 124. As shown in FIG. 4, first lens 404 can be arranged such that the face of each optical fiber of fiber bundle 124 coincides with the focal length of first lens 404, and emits a reference beam from a point that is a particular radial distance from the optical axis of first lens 404. In some embodiments, if spatial separator 402 is used to arrange the optical fibers of fiber bundle 124 in a straight line, such that the reference beams emitted by the optical fibers are all co-planar, spatial separator 402 can be positioned with respect to first lens 404 such that the optical axis of first lens 404 is on the same plane as the reference beams. For example, this arrangement can facilitate alignment of one or more other components with spatial separator 402 and first lens 404.

In some embodiments, optical fibers of fiber bundle 124 can emit an individual reference beam toward a first side of first lens 404, which can focus the light received from fiber bundle 124 at one focal length f on a distal side of first lens 404. This can cause the reference beams from each of the various optical fibers to converge at the focal point of first lens 404. In the absence of other optical components, these reference beams diverge again after the focal point such that at a distance 2*f from the face of the optical fibers the reference beams are mirrored across the optical axis and can be collected by an array of optical fibers having mirror image positions to the optical fibers positioned by spatial separator 402.

In some embodiments, free space mixer 400 can include a beam splitter 406 arranged at a focal point of first lens 404, and at focal points of a second lens 412, a third lens 420, and a fourth lens 430. In some embodiments, beam splitter 406 can receive light from first lens 404, and can redirect a first portion of the light toward third lens 420, and can transmit a second portion of the light toward fourth lens 430. For example, about half of the light received from first lens 404 can be redirected toward third lens 420 and about half the light received from first lens 404 can be transmitted toward fourth lens 430.

In some embodiments, free space mixer 400 can include a second spatial separator 410 that is configured to mechanically position the distal end of various optical fibers in an optical fiber bundle (e.g., optical fiber bundle 118) such that a face of each optical fiber is held at a particular position and orientation relative to other optical components of free space mixer 400. In some embodiments, spatial separator 410 can be implemented using any suitable components, such as components described above in connection with spatial separator 302 of FIG. 3.

In some embodiments, second lens 412 can be optically coupled to the optical fibers of fiber bundle 118. As shown in FIG. 4, second lens 412 can be arranged such that the face of each optical fiber of fiber bundle 118 coincides with the focal length of second lens 412, and emits a backscattered beam from a point that is a particular radial distance from the optical axis of second lens 412. In some embodiments, if spatial separator 410 is used to arrange the optical fibers of fiber bundle 118 in a straight line, such that the backscattered beams emitted by the optical fibers are all co-planar, spatial separator 410 can be positioned with respect to second lens 412 such that the optical axis of second lens 412 is on the same plane as the backscattered beams. For example, this arrangement can facilitate alignment of one or more other components with spatial separator 410 and second lens 412.

In some embodiments, optical fibers of fiber bundle 118 can emit an individual backscattered beam toward a first side of second lens 412, which can focus the light received from fiber bundle 118 at one focal length f on a distal side (distal relative to light source 102) of second lens 410. This can cause the backscattered beams from each of the various optical fibers to converge at the focal point of second lens 412. In the absence of other optical components, these backscattered beams diverge again after the focal point such that at a distance 2*f from the face of the optical fibers the backscattered beams are mirrored across the optical axis and can be collected by an array of optical fibers having mirror image positions to the optical fibers positioned by spatial separator 410.

In some embodiments, beam splitter 406 can receive light from second lens 412, and can redirect a first portion of the light toward fourth lens 430, and can transmit a second portion of the light toward third lens 420. For example, about half of the light received from second lens 412 can be redirected toward fourth lens 430 and about half the light received from second lens 412 can be transmitted toward third lens 420.

In some embodiments, reference beams emitted by first lens 404 can converge at the interface of beam splitter 406, and backscattered beams emitted by second lens 412 can converge at the interface of beam splitter 406 from an orthogonal direction. Beam splitter 406 can split the reference beams emitted by first lens 404, and first reference beams can be transmitted by beam splitter 406 and can diverge as the first reference beams travel toward a first side of fourth lens 430, and second reference beams can be reflected by beam splitter 406 and can diverge as the second reference beams travel toward a first side of third lens 420. Beam splitter 406 can split the backscattered beams emitted by second lens 412, and first backscattered beams can be transmitted by beam splitter 406 and can diverge as the first backscattered beams travel toward the first side of third lens 420, and second backscattered beams can be reflected by beam splitter 406 and can diverge as the second backscattered beams travel toward the first side of fourth lens 430. In some embodiments, spatial separator 402, first lens 404, spatial separator 410, second lens 412, and beam splitter 406 can be aligned such that the first reference beams combine with corresponding first backscattered beams to form first interference beams that diverge toward the first side of third lens 420, and the second reference beams combine with corresponding second backscattered beams to form second interference beams that diverge toward the first side of fourth lens 430. In some embodiments, first interference beams can include interference fringes caused by an interaction between the reference light and the backscattered light included in the beam.

In some embodiments, third lens 420 and fourth lens 430 can be arranged such that the interface of beam splitter 406 coincides with focal length f of third lens 420 and fourth lens 430. In some embodiments, third lens 420 can focus the first interference beams such that the first interference beams form substantially parallel beams traveling parallel to the optical axis of third lens 420, and fourth lens 430 can focus the second interference beams such that the second interference beams form substantially parallel beams traveling parallel to the optical axis of fourth lens 430. In some embodiments, the reference arm can include a polarization controller (not shown) to cause the light emitted from fiber bundle 124 to be uniformly polarized such that substantially all of the light emitted from fiber bundle 124 has the same polarization as the backscattered beams. For example, a polarization controller can be inserted on optical fiber 120. In general, as light in the reference and sample arms propagates in optical fibers (e.g., optical fiber 106, optical fiber 120, optical fibers in fiber bundle 110, optical fibers in fiber bundle 118, and optical fibers in fiber bundle 124), the polarization can change arbitrarily due to physical characteristics of the fiber (e.g., caused by bending or stress induced on the fiber). Additionally, a 90° polarization change is added in the sample arm to induce reflection by polarizing beam splitter 306). Manipulation of a polarization controller in the reference arm can be used to match the polarization of the light in the reference arm to the polarization of backscattered beams in the sample arm to increase the interaction of the beams in the free space mixer.

In some embodiments, free space mixer 400 can include a third spatial separator 422 that is configured to mechanically position the proximal end of various optical fibers in an optical fiber bundle (e.g., optical fiber bundle 132-1) such that a face of each optical fiber is held at a particular position and orientation relative to other optical components of free space mixer 400. For example, the core of each individual optical fiber of optical fiber bundle 132-1 can be positioned by placing the cladding surrounding the core into a v-shaped groove of third spatial separator 422 that is sized to precisely position an individual optical fiber including a core and cladding. Additionally, in some embodiments, free space mixer 400 can include a fourth spatial separator 432 that is configured to mechanically position the proximal end of various optical fibers in an optical fiber bundle (e.g., optical fiber bundle 132-2) such that a face of each optical fiber is held at a particular position and orientation relative to other optical components of free space mixer 400. For example, the core of each individual optical fiber of optical fiber bundle 132-2 can be positioned by placing the cladding surrounding the core into a v-shaped groove of fourth spatial separator 432 that is sized to precisely position an individual optical fiber including a core and cladding.

In some embodiments, spatial separators 422 and 432 can be implemented using any suitable components, such as components described above in connection with spatial separator 302. In some embodiments, spatial separator 422 can be positioned such that the first interference beams emitted from beam splitter 406 are each received by a corresponding optical fiber, and spatial separator 432 can be positioned such that the second interference beams emitted from beam splitter 406 are each received by a corresponding optical fiber. As described below, an alignment system can be used to precisely align spatial separators 422 and 432 such that the interference beams are received at corresponding optical fibers, which can convey the interference light to a detector. Note that in general the fringes output to a fiber in fiber bundle 132-1 and the corresponding fiber in fiber bundle 132-2 initially have the same polarization and are 180 degrees out of phase (e.g., a phase shift caused in part by beam splitter 406). As the light propagates from mixer 400 the polarization in each fiber may diverge from one another (e.g., for single mode fibers, a polarization of the light in a fiber in fiber bundle 132-1 may diverge from a polarization of the light in the corresponding fiber of fiber bundle 132-2), while the phase relationship between the two signals is generally maintained. This can facilitate suppression of a DC-noise component, and can amplify the signal encoded in the fringe using a balanced detector.

Figure 5:
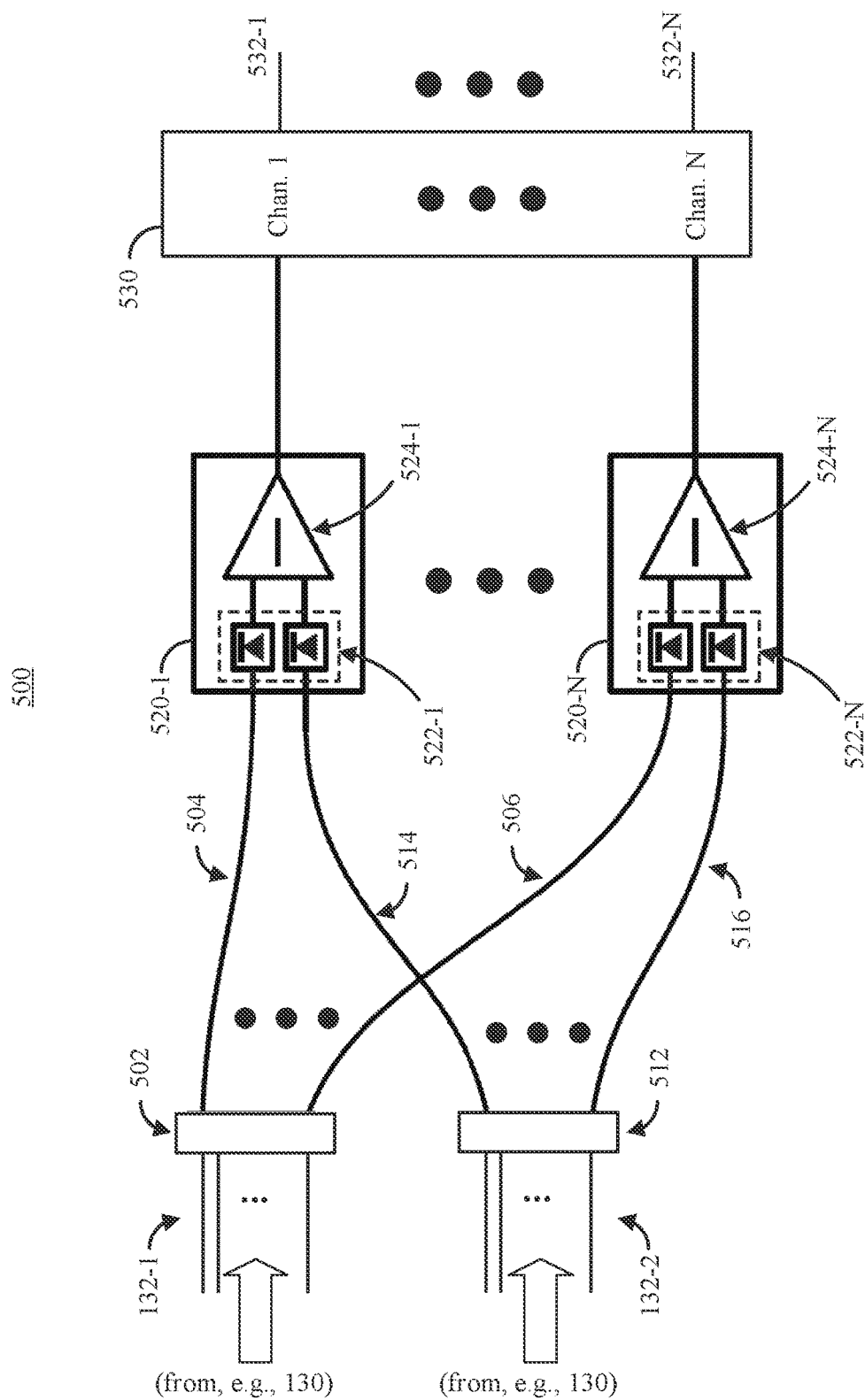
FIG. 5 shows an example of components that can be used to implement a portion of a detector for multiple beam optical coherence tomography in accordance with some embodiments of the disclosed subject matter.

FIG. 5 shows an example 500 of components that can be used to implement a portion of a detector for multiple beam optical coherence tomography in accordance with some embodiments of the disclosed subject matter. As shown in FIG. 5, detector 500 can be implemented using various components. In some embodiments, detector 500 can include a first optical junction 502 that can be used to couple various optical fibers in an optical fiber bundle (e.g., optical fiber bundle 132-1) to up to N individual optical fibers 504 to 506, and a second optical junction 512 that can be used to couple various optical fibers in an optical fiber bundle (e.g., optical fiber bundle 132-2) to up to N individual optical fibers 514 to 516. In some embodiments, any suitable component or components can be used to implement first optical junction 502 and/or second optical junction 512. For example, optical junction 502 and/or optical junction 512 can be implemented using a junction box. As another example, each optical fiber of fiber bundle 132-1 and/or fiber bundle 132-2 can be coupled to a connector that can be mechanically coupled with a corresponding connector coupled to individual fibers 504 to 506 and/or 514 to 516 to optically couple the corresponding optical fibers. In some embodiments, optical junction 502 and/or optical junction 512 can be omitted. For example, individual fibers of fiber bundle 132-1 and/or fiber bundle 132-2 can be terminated with a connector and coupled to corresponding detectors. In some embodiments, fiber bundle 132-1 and/or fiber bundle 132-2 can be positioned such that light emitted by each fiber/waveguide of the bundle is directed toward a corresponding detector element (e.g., of detectors 520-1 through 520-N) without requiring intermediate, separate fibers 504 to 506 and/or 514 to 516.

In some embodiments, detector 500 can include N balanced detectors 520-1 to 520-N. As shown in FIG. 5, in some embodiments, each balanced detector 520 can be coupled to a pair of optical fibers carrying interference fringes from a mixer (e.g., mixer 130). In the example shown in FIG. 5, the two interference fringes received by a particular balanced detector 520 were generated using the same backscattered signal.

In some embodiments, each balanced detector 520 can include a pair of balanced photodetectors 522 that generate individual output signals that are provided to a subtractor circuit 524 that subtracts one input from the other to reduce common mode noise present in both interference fringes. Subtractor circuit 524 can output a fringe signal to a channel of a digital acquisition board 530 that includes at least N channels. In some embodiments, digital acquisition board 530 can output fringe signals that can be used generate OCT data that is indicative of the structure of the sample at the location at which each beam was backscattered from the sample.

In some embodiments, a balanced detection operation can be implemented digitally (e.g., in lieu of using balanced detectors 520). For example, fiber bundle 132-2 and associated components can be omitted, and single detectors (e.g., a single photodetector) can be optically coupled to each fiber/waveguide of fiber bundle 132-1 (e.g., in lieu of balanced detectors 520). In such an example, one or more beams from fiber bundle 124 can be optically coupled to one or more fibers 132-1 without being mixed with a corresponding beam from fiber bundle 118, such that at least one fiber in fiber bundle 132-1 conveys only reference arm light (e.g., with other fibers of fiber bundle 132-1 conveying fringe signals). In a more particular example, one or more fiber from fiber bundle 118 are not connected to mixer 130. As another more particular example, fiber bundle 124 can include more fibers than fiber bundle 118, such that the reference arm has more beams than the sample arm. One or more detectors (e.g., reference detectors) can be optically coupled to a fiber/waveguide of fiber bundle 132-1 that includes only reference arm light, and can be used to record the intensity of the reference arm light concurrently with other detectors recording intensity of fringe signals (e.g., fringe detectors). As another more particular example, in addition to or in lieu of the previous examples, a portion of light output by light source 102 (e.g., 1%, 2%, etc.) can be directed to one or more reference detectors without passing through the reference arm or sample arm to provide a signal that is substantially similar to reference arm signals in fibers of fiber bundle 132-1. A digitized signal from the reference detector can be subtracted from digitized signals from the fringe detectors to remove noise (e.g., noise caused by fluctuations in laser power) fringe signals digitized on the remaining detectors.

FIGS. 6A and 6B show top-down and side views of an example 600 of an arrangement of components that can be used to align multiple optical fibers across a free space gap in accordance with some embodiments of the disclosed subject matter. In some embodiments, strong optical coupling between the various components used to generate beams for interrogating the sample and creating interference fringes in free-space using techniques described herein can require very precise alignment of components. In some embodiments, alignment components 600 can be used to align a beam forming optical fiber(s) (e.g., an optical fiber 602) with a focusing component (e.g., a lens 606-1), and an assembly of optical fiber 602 and lens 606-1 with a corresponding assembly of optical fiber 620 and lens 606-2.

In some embodiments, an optical fiber 602 can be mechanically coupled to a 6-axis stage 608-1 via a spatial separator 604-1. This can maintain an orientation of the beam forming face of optical fiber 602 and 6-axis stage 608-1, which can allow the direction of the beam emitted by optical fiber 602 to be adjusted with respect to other components alignment components 600. In some embodiments, spatial separator 604-1 can affix the orientation of a group of optical fibers with respect to each other, and with respect to 6-axis stage 608-1 such that the direction of beams emitted by the various optical fibers can be adjusted as a unit.

In some embodiments, 6-axis stage 608-1 can be mechanically coupled to lens 606-1 via a jig 610-1, and jig 610-1 can be mounted to a tile/rotation stage 612-1, which can be mounted to a linear stage 614-1. In some embodiments, adjustments can be made to the position of jig 610-1 using tile/rotation stage 612-1 and/or linear stage 614-1 without changing the relative orientation of lens 606-1 and optical fiber 604-1. In some embodiments, alignment components 600 can be used to adjust the alignment of optical fiber 602 and optical fiber 620 to ensure that a beam emitted from optical fiber 602 is received by optical fiber 620. Additionally, in some embodiments, a power meter can be associated with each of multiple fiber channels associated with an output side of the alignment components (e.g., optical fiber 620 and at least one other optical fiber), and adjustments can be made to the position of jig 610-1 using tile/rotation stage 612-1 and/or linear stage 614-1, and/or to the relative orientation of lens 606-1 and optical fiber 604-1 until the overall optical power from all fiber channels is maximized.

In a particular example in which each spatial separator 604 positions eight optical fibers, spatial separator 604 can be mounted to 6-axis stage 608, which can control the relative position and angle (e.g., yaw and pitch) of optical fibers secured by spatial separator 604 with respect to the optical lens 606, which can provide 8 collimated beams whose aperture stop is located at one focal length distance away from lens 606. Controlling the roll of the stage, an axis of spatial separator 604 (e.g., an imaginary line that intersects the fiber cores in a V-groove assembly) to an axis of a spatial separator of an opposite beam receiving component. The alignment between 6-axis stage 608 and lens 606 can be secured by jig 610, which is mounted on tilt and rotation stage 612. The manipulation of tilt and rotation stage 612 can allow the global alignment of the 8 radiations. Linear translation stage 614 can be used to match the distance between the lenses 606 to an appropriate distance (e.g., twice the focal length when the lenses have the same focal length) so that the 8 radiations on one end face of spatial separator 604 can be reliably coupled optical fibers position by a downstream spatial separator.

In some embodiments, alignment components 600 can be used to align various optical components that can be used in connection with the mechanisms described herein. For example, alignment components 600 can be used to align spatial separator 302, first lens 304, fifth lens 320, and spatial separator 322 to ensure that beams emitted by optical fibers in fiber bundle 110 are optically coupled to corresponding optical fibers in fiber bundle 118. As another example, alignment components 600 can be used to align the component of mixer 400.

Figure 7A:
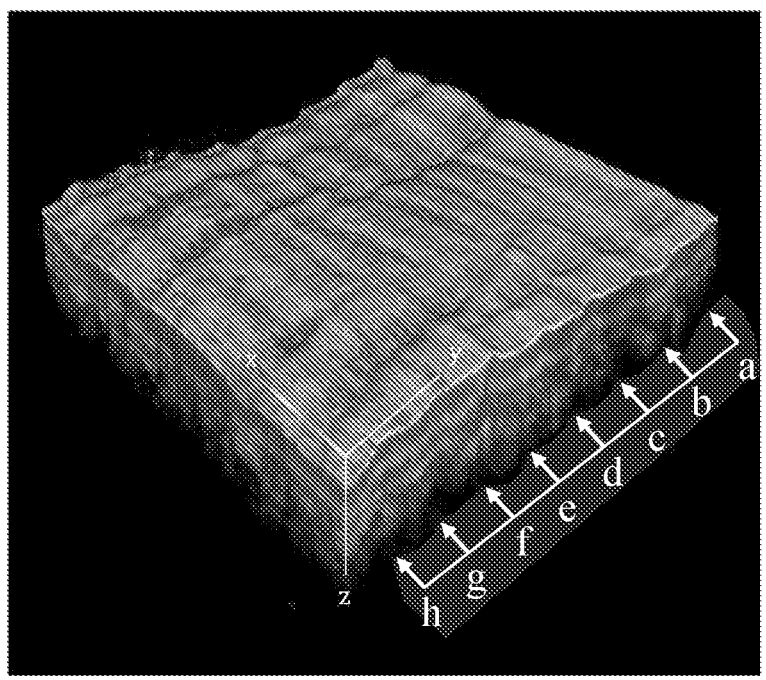
FIG. 7A shows an example if a composite structural C-scan of a human finger generated by combining information from multiple optical coherence tomography signals obtained simultaneously using a system for multiple beam optical coherence tomography implemented in accordance with some embodiments of the disclosed subject matter.
Figure 7B:
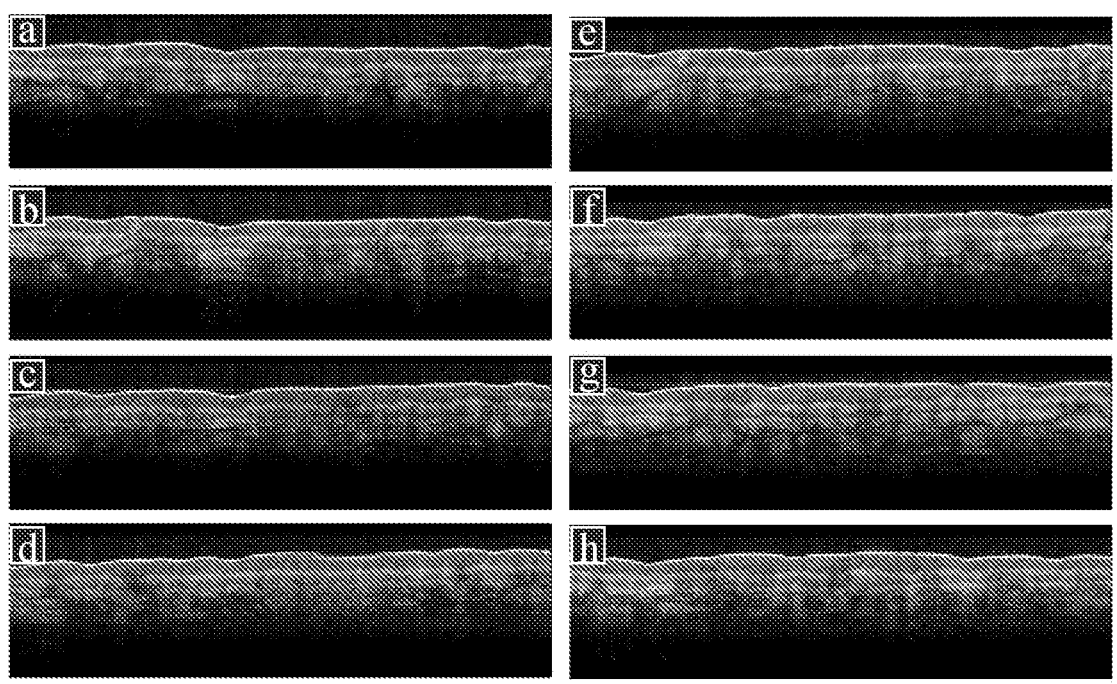
FIG. 7B shows examples of B-scans generated simultaneously using different channels of a system for multiple beam optical coherence tomography implemented in accordance with some embodiments of the disclosed subject matter.

FIG. 7A shows an example of a composite structural C-scan of a human finger generated by combining information from multiple optical coherence tomography signals shown in FIG. 7B that were obtained simultaneously using a system for multiple beam optical coherence tomography implemented in accordance with some embodiments of the disclosed subject matter. As shown in FIG. 7B, multiple B-scans shown in panels (a) to (h) were captured simultaneously using an OCT system implemented in accordance with some embodiments of the disclosed subject matter. The information in various B-scans can be combined to generate a C-scan depicting a larger area of the sample.

Figure 8:
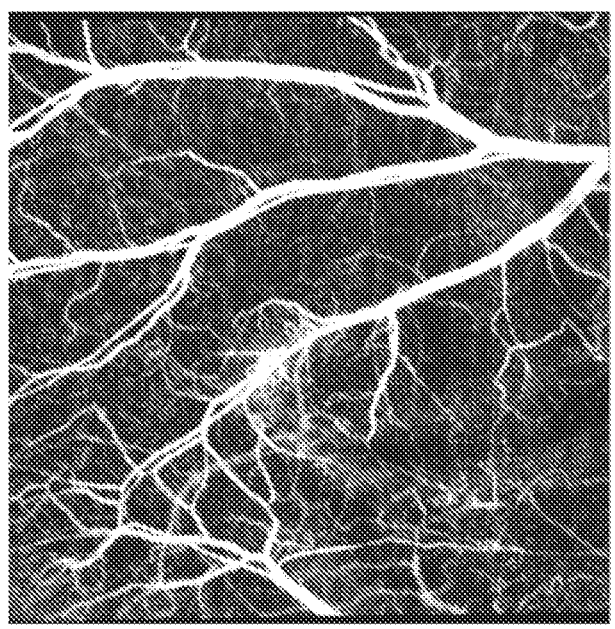
FIG. 8 shows an example of multiple enface optical coherence tomography angiography images of an interior of a mouse ear generated simultaneously using different channels of a system for multiple beam optical coherence tomography implemented in accordance with some embodiments of the disclosed subject matter and a composite enface image generated from information generated using the different channels in accordance with some embodiments of the disclosed subject matter.
Figure 8:
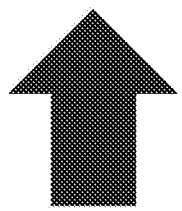
Figure 8:
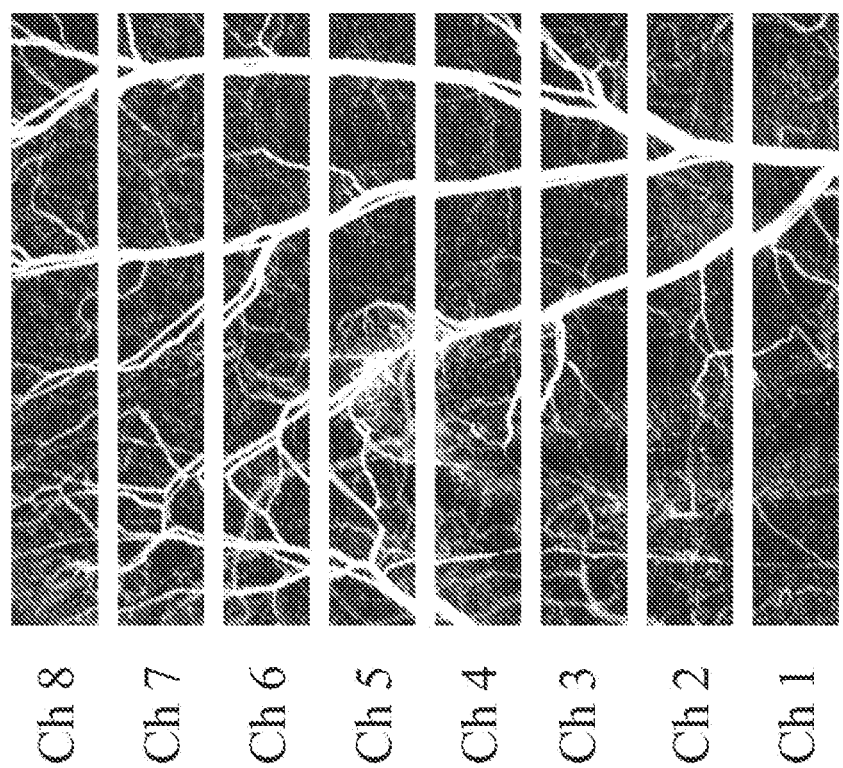

FIG. 8 shows an example of multiple enface optical coherence tomography angiography images of an interior of a mouse ear generated simultaneously using different channels of a system for multiple beam optical coherence tomography implemented in accordance with some embodiments of the disclosed subject matter and a composite enface image generated from information generated using the different channels in accordance with some embodiments of the disclosed subject matter.

Figure 9:
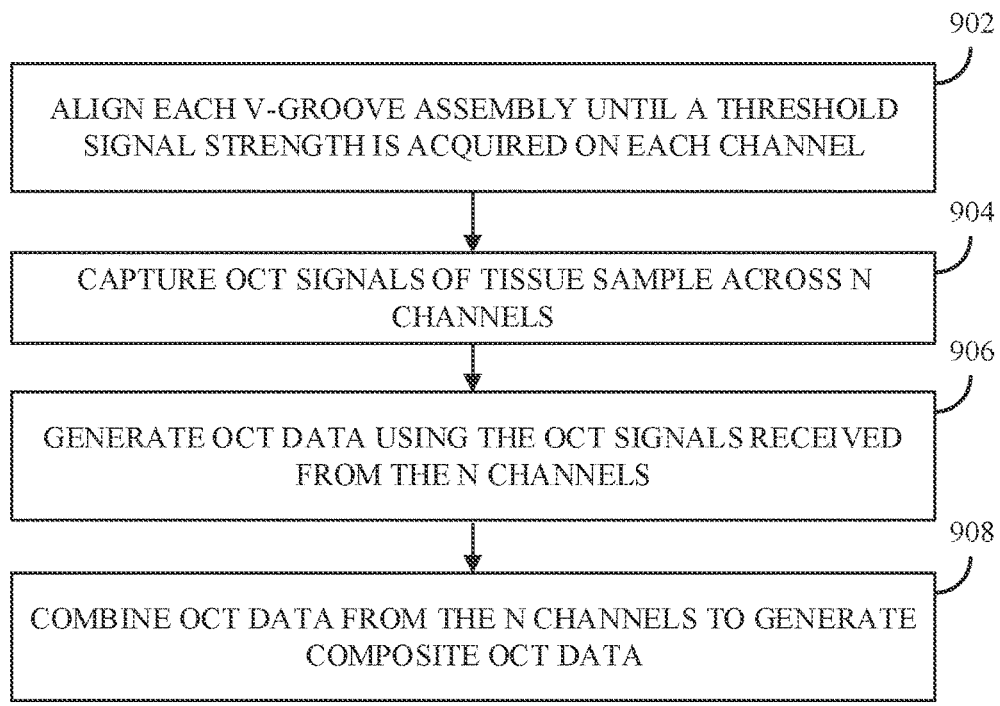
FIG. 9 shows an example of a process for simultaneously generating multiple optical coherence tomography images using multiple beams in accordance with some embodiments of the disclosed subject matter.

FIG. 9 shows an example 900 of a process for simultaneously generating multiple optical coherence tomography images using multiple beams in accordance with some embodiments of the disclosed subject matter. In some embodiments, process 900 can begin at 900, by aligning each v-groove assembly and corresponding lens of a multiple beam optical coherence tomography system to a specific performance level. For example, the alignment can be adjusted until the optical coupling between each pair of optical fibers across a free space portion of the system (e.g., between fiber bundle 110 and fiber bundle 118, or between fiber bundle 118 fiber bundles 132-1 and 132-2) allows for a received signal strength at the detectors for each channel to be above a threshold (e.g., using a calibration surface such as an optical mirror).

In some embodiments, process 900 can use signals received by one or more detectors (e.g., detector 134 and/or detectors 520) as a feedback signal that can be used to adjust the orientation and/or position of various components of the system.

At 904, process 900 can include capturing OCT signals of a tissue sample across N channels simultaneously. For example, OCT signals can be captured using mechanisms described herein across N channels simultaneously using a free-space interferometer using techniques described above.

In some embodiments, process 900 can capture fringe signals corresponding to multiple A-scans while N beams are scanned across a sample (e.g., via translation of the sample, translation of the optics, and/or scanning via a galvo scanner).

In some embodiments, process 900 can generate OCT data using the OCT signals received from the N channels. For example, process 900 can convert the fringe signals received at 904 into A-scans, and can combine A-scans from a particular channel into B-scans.

At 908, process 900 can combine OCT data from the N channels to generate composite OCT data depicting a structure of the sample across a larger are than is captured using a single channel. In some embodiments, process 900 can account for relatively small differences in the N channels while combining the data. For example, process 900 can shift a B-scan from each channel axially by an amount corresponding to a path length difference of a particular channel from a reference path length.

Figure 10:
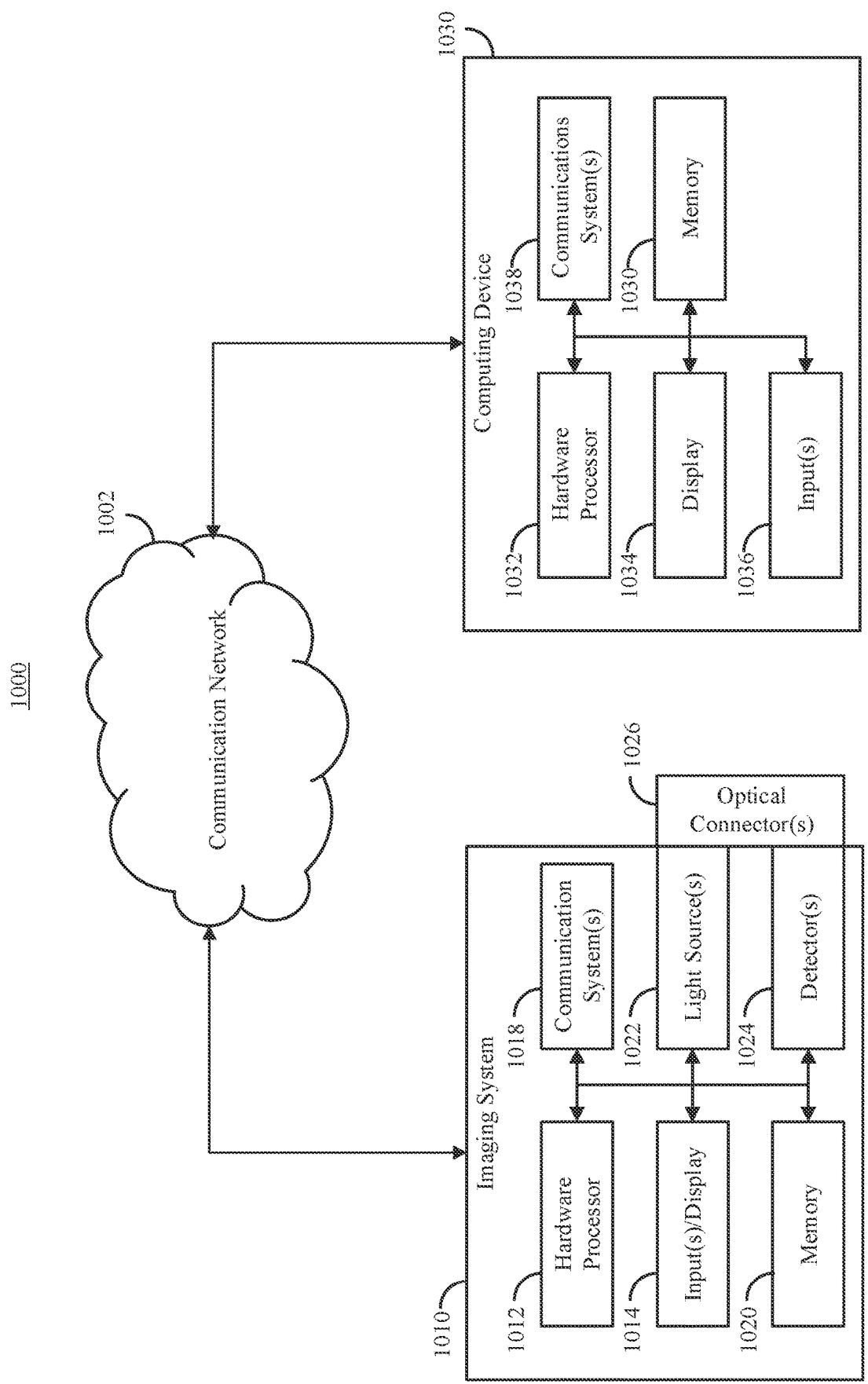
FIG. 10 shows an example of hardware that can be used to implement an imaging device and/or a computing device that can be used in connection with some embodiments of mechanisms for multiple beam optical coherence tomography implemented in accordance with some embodiments of the disclosed subject matter.

FIG. 10 shows an example 1000 of hardware that can be used to implement an imaging device and/or a computing device that can be used in connection with some embodiments of mechanisms for multiple reference arm spectral domain optical coherence tomography implemented in accordance with some embodiments of the disclosed subject matter. For example, hardware shown in FIG. 10 can be used to implement at least a portion of a system for multiple beam optical coherence tomography (e.g., system 100). As shown in FIG. 10, in some embodiments, an imaging system 1010 can include a hardware processor 1012, a user interface and/or display 1014, one or more communication systems 1018, memory 1020, one or more light sources 1022, one or more electromagnetic detectors 1026, and/or one or more optical connectors 1026. In some embodiments, hardware processor 1012 can be any suitable hardware processor or combination of processors, such as a central processing unit (CPU), a graphics processing unit (GPU), a microcontroller (MCU), a field programmable gate array (FPGA), a dedicated image processor, etc. In some embodiments, input(s) and/or display 1014 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc.

In some embodiments, communications systems 1018 can include any suitable hardware, firmware, and/or software for communicating information over a communication network 1002 and/or any other suitable communication networks. For example, communications systems 1018 can include one or more transceivers, one or more communication chips and/or chip sets, etc. In a more particular example, communications systems 1018 can include hardware, firmware and/or software that can be used to establish a Wi-Fi connection, a Bluetooth connection, a cellular connection, an Ethernet connection, an optical connection, etc.

In some embodiments, communication network 1002 can be any suitable communication network or combination of communication networks. For example, communication network 1002 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 1002 can be a local area network, a wide area network, a public network (e.g., the Internet), a private or semi-private network (e.g., a corporate or university intranet), any other suitable type of network, or any suitable combination of networks. Communications links shown in FIG. 10 can each be any suitable communications link or combination of communications links, such as wired links, fiber optic links, Wi-Fi links, Bluetooth links, cellular links, etc.

In some embodiments, memory 1020 can include any suitable storage device or devices that can be used to store instructions, values, etc., that can be used, for example, by hardware processor 1012 to process image data generated by one or more optical detectors, to present content using input(s)/display 1014, to communicate with a computing device 1030 via communications system(s) 1018, etc. Memory 1020 can include any suitable volatile memory, non-volatile memory, storage, any other suitable type of storage medium, or any suitable combination thereof. For example, memory 1020 can include RAM, ROM, EEPROM, one or more flash drives, one or more hard disks, one or more solid state drives, one or more optical drives, etc. In some embodiments, memory 1020 can have encoded thereon a computer program for controlling operation of imaging system 1010. In some such embodiments, hardware processor 1012 can execute at least a portion of the computer program to control one or more light sources and/or detectors (e.g., to capture OCT data as described above in connection with FIG. 9), to generate images and/or calculate values (e.g., an OCT image, etc.), transmit and/or receive information to/from computing device 1030, combine OCT images from different channels to generate composite OCT images (e.g., as described above in connection with FIGS. 7-9), etc.

In some embodiments, imaging system 1010 can include one or more light sources 1022, such a coherent or incoherent light source (e.g., a laser, a light emitting diode or combination of light emitting diodes, a white light source, etc.), which can be a broadband light source, or a narrower band light source. For example, the bandwidth of the light source can be selected to provide a range of wavelengths that facilitates depth detection over a maximum imaging range of the OCT system. Additionally, in some embodiments, light sources 1022 can be associated with one or more filters.

In some embodiments, imaging system 1010 can include one or more light detectors 1024, such as one or more photodiodes (e.g., balanced detectors 520), and/or one or more image sensors (e.g., a CCD image sensor or a CMOS image sensor, either of which may be a linear array or a two-dimensional array). For example, in some embodiments, detectors 1024 can include one or more detectors configured to detect light at specific wavelengths (e.g., using filters, using optics to guide light of different wavelengths to different portions of the detector(s), etc.)

In some embodiments, imaging system 1010 can include one or more optical connectors 1026. For example, such optical connectors can be fiber optic connectors configured to form an optical connection between light source(s) 1022 and/or detector 1024 and an optical fiber (e.g., as part of a fiber optic cable). For example, optical connectors 1026 can be used to couple light source 1022 to a sample arm and reference arm of system 100 via a fiber coupler (e.g., fiber coupler 104).

In some embodiments, computing device 1030 can include a hardware processor 1032, a display 1034, one or more inputs 1036, one or more communication systems 1038, and/or memory 1040. In some embodiments, hardware processor 1032 can be any suitable hardware processor or combination of processors, such as a CPU, a GPU, an MCU, an FPGA, a dedicated image processor, etc. In some embodiments, display 1034 can include any suitable display devices, such as a computer monitor, a touchscreen, a television, a transparent or semitransparent display, a head mounted display, etc. In some embodiments, inputs 1036 can include any suitable input devices and/or sensors that can be used to receive user input, such as a keyboard, a mouse, a touchscreen, a microphone, a gaze tracking system, motion sensors, etc.

In some embodiments, communications systems 1038 can include any suitable hardware, firmware, and/or software for communicating information over communication network 1002 and/or any other suitable communication networks. For example, communications systems 1038 can include one or more transceivers, one or more communication chips and/or chip sets, etc. In a more particular example, communications systems 1038 can include hardware, firmware and/or software that can be used to establish a Wi-Fi connection, a Bluetooth connection, a cellular connection, an Ethernet connection, etc.

In some embodiments, memory 1040 can include any suitable storage device or devices that can be used to store instructions, values, etc., that can be used, for example, by hardware processor 1032 to present content using display 1034, to communication with one or more imaging devices, etc. Memory 1040 can include any suitable volatile memory, non-volatile memory, storage, any other suitable type of storage medium, or any suitable combination thereof. For example, memory 1040 can include RAM, ROM, EEPROM, one or more flash drives, one or more hard disks, one or more solid state drives, one or more optical drives, etc. In some embodiments, memory 1040 can have encoded thereon a computer program for controlling operation of computing device 1030. In such embodiments, hardware processor 1032 can execute at least a portion of the computer program to receive content (e.g., image content) from one or more imaging devices (e.g., imaging device 1010), combine OCT images from different channels to generate composite OCT images (e.g., as described above in connection with FIGS. 7-9), present content (e.g., images and/or values,) transmit content to one or more other computing devices and/or imaging systems, etc.

In some embodiments, computing device 1030 can be any suitable computing device, such as a general purpose computer or special purpose computer. For example, in some embodiments, computing device 1030 can be a smartphone, a wearable computer, a tablet computer, a laptop computer, a personal computer, a server, etc. As another example, in some embodiments, computing device 1030 can be a medical device, a system controller, etc.

Figure 11:
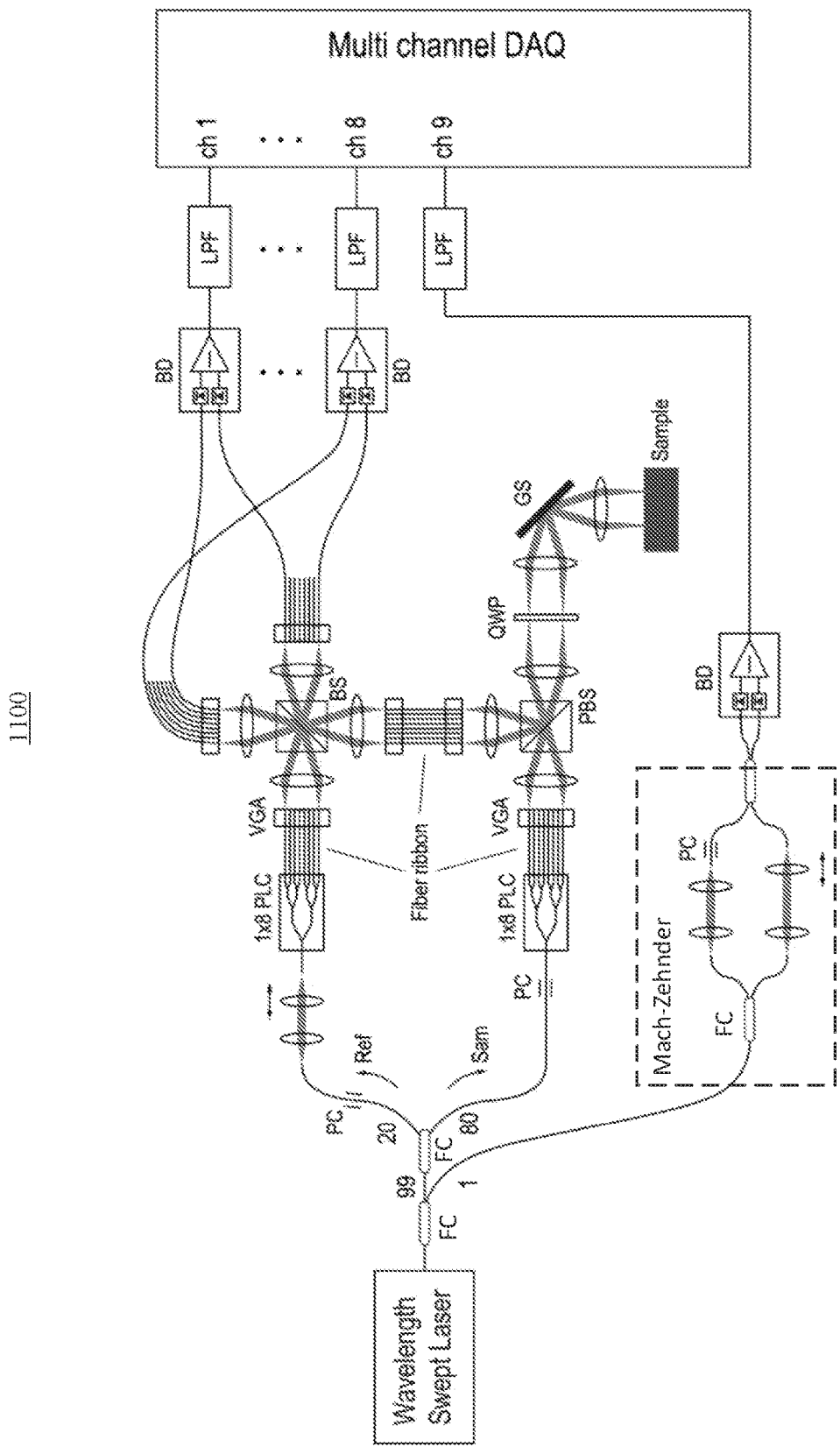
FIG. 11 shows an example of a system for multiple beam optical coherence tomography implemented in accordance with some embodiments of the disclosed subject matter.

FIG. 11 shows an example 1100 of a system for multiple beam optical coherence tomography implemented in accordance with some embodiments of the disclosed subject matter. System 1100 includes a custom-built wavelength-swept laser operating at 125 kHz A-scan rate with center wavelength at 1300 nm. One percent of the laser output is directed to a Mach-Zehnder interferometer (MZI) in order to generate a calibration vector for linear k-space resampling. The remaining 99% of the output is delivered to a multibeam OCT interferometer. In the reference arm, a 1×8 PLC splitter (available from FS headquartered in New Castle, Delaware) is used to divide the input into 8 fields which were transmitted along 8 optical fiber ribbon and delivered to a V-groove assembly (VGA) (available from OZ Optics) with 250 micrometer (μm) fiber spacing. In the sample arm, after passing a 1×8 PLC, 8 sample fields are relayed from a VGA end face to 8 focal spots displaced by 850 μm on the sample plane by the two telescopes in a multibeam microscope. The microscope design was optimized using ZEMAX simulation to provide diffraction-limited focal spot over a 6.8×6.8 mm field-of-view. A polarization beam splitter (PBS) is used to align the polarization states of the illumination beams to a single state and double passing through the quarter-wave plate (QWP) changed the polarization states of the returning beams to be orthogonal to the input states, thus the beams are reflected at the PBS and coupled to an additional fiber ribbon through which the beams are delivered to a detection part. Each of the 8 reference and sample fields arriving at the beam splitter (BS) create 8 interference fringes and those in each arm of the BS are coupled to VGAs for balanced detection. The 8 fringes are acquired through the first 8 channels of a 16-channel data acquisition board (AlazarTech). The MZI signal is acquired through the ninth channel of the board.

Path length differences of the 8 channels of system 1100 are shown below in Table 1. The path-length differences are attributed to the non-uniform fiber lengths in the ribbon and different optical path-length for each beam to travel in the microscope. The maximum path-length difference was approximately 200 μm, which is one order of magnitude smaller than the ranging depth of the system. The microscope design gave sufficient aberration correction and the measured coupling efficiency of the returning beams into the fiber ribbon was 68.5%. The system sensitivities were 92.13±1.13 dB at 3.7 mW average power incident on the sample for each channel. The sensitivity variation between the channels is due in large part to polarization dispersion in the fiber ribbon, resulting in channel-dependent polarization mismatch between the reference and sample fields.

optical fiber 1208. As another example, more than half of source light received at fiber coupler 1204 can be directed toward optical fiber 1206 or optical fiber 1208, and less than half can be directed toward the other optical fiber.

In some embodiments, optical fiber 1206 can be optically coupled to a first phase modulator 1210, such that a first portion of light received at fiber coupler 1204 is provided to an input of phase modulator 1210. Additionally, in some embodiments, optical fiber 1208 can be optically coupled to a second phase modulator 1212, such that a second portion of light received at fiber coupler 1204 is provided to an input of phase modulator 1212.

Figure 12:
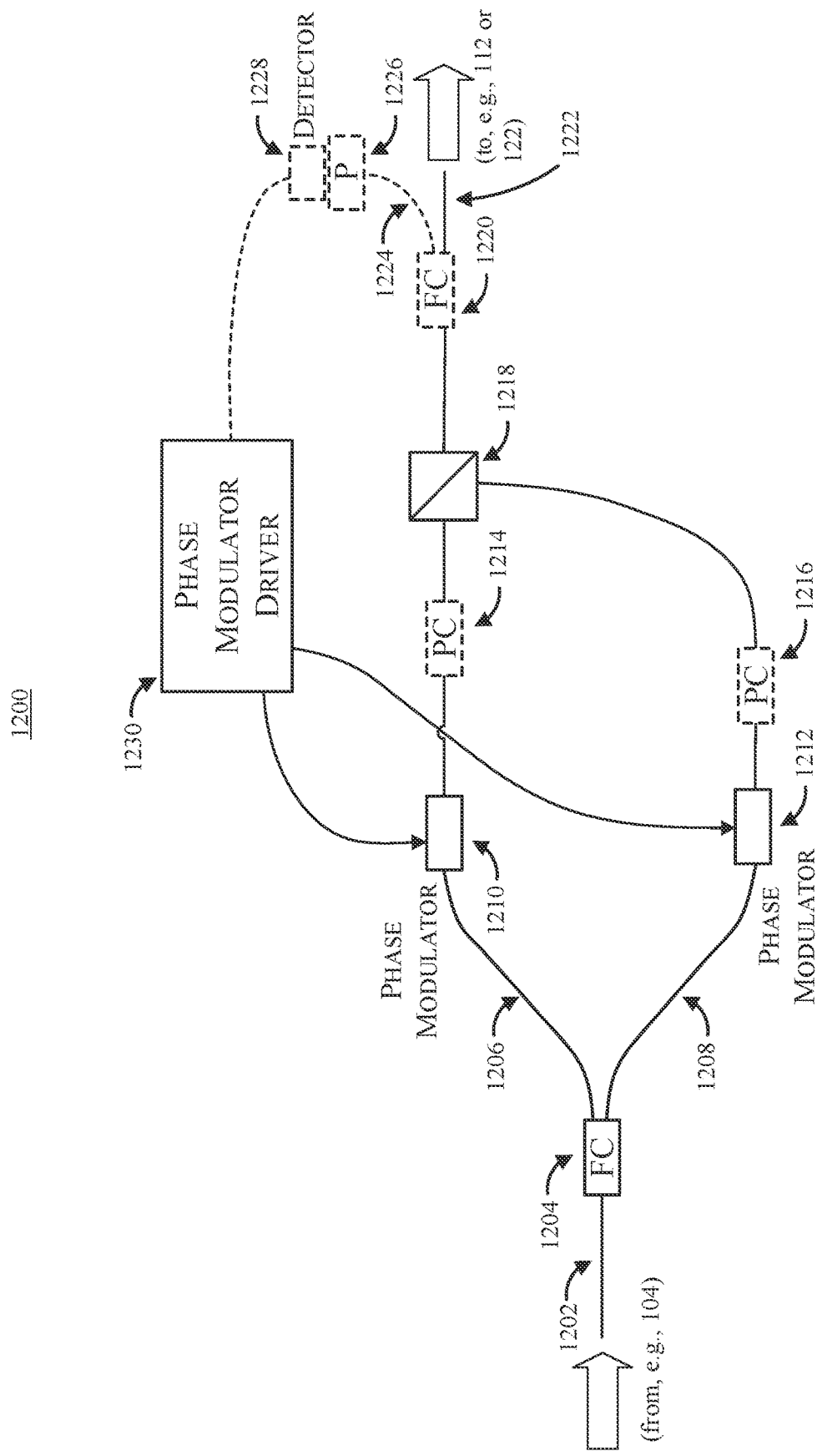
FIG. 12 shows an example of components that can be used to implement a portion of a phase and/or polarization modulator in accordance with some embodiments of the disclosed subject matter.

In some embodiments, optical modulator 1210 and optical modulator 1212 can be optically coupled to a polarization beam combiner 1218. As shown in FIG. 12, a polarization controller 1214 can be disposed between phase modulator 1210 and polarization beam combiner 1218. In some embodiments, polarization controller 1214 can align the polarization state to a first polarization state at the polarization beam combiner 1218. Additionally or alternatively, a polarization controller 1216 can be disposed between phase modulator 1212 and polarization beam combiner 1218. In some embodiments, polarization controller 1216 can align the polarization state to a second polarization state at the polarization beam combiner 1218.

TABLE 1

| Channel | 1 | 2 | 3 | 4 | 5 | 6 | 7 | 8 |
|---|---|---|---|---|---|---|---|---|
| Path-length difference relative to channel 1 (μm) | — | 110 | 90 | 310 | 135 | 150 | 205 | 90 |
| Sensitivity (dB) | 91.26 | 93.26 | 91.00 | 93.15 | 93.26 | 93.02 | 93.01 | 92.62 |

FIG. 12 shows an example 1200 of components that can be used to implement a portion of a phase and/or polarization modulator in accordance with some embodiments of the disclosed subject matter. In some embodiments, modulation components 1200 can provide phase modulation and/or polarization modulation using multiple phase modulators. In some embodiments, modulation component 142 and/or modulation component 144 can be implemented using modulation components 1200.

As shown in FIG. 12, a fiber coupler 1204 can be coupled to an electromagnetic waveguide 1202 (e.g., an optical fiber) of the sample arm or the reference arm (e.g., the sample arm or reference arm of system 100). For example, optical fiber 1202 can optically couple an input of fiber coupler 1204 to a light source (e.g., via an optical coupler between fiber coupler 1204 and a light source, such as light source 102). In some embodiments, fiber coupler 1204 can receive light from a light source (e.g., via an electromagnetic waveguide, such as an optical fiber, and/or other optical components, such as a fiber coupler, optically coupled between an output of light source 102 and an input port of fiber coupler 1204), and can output a first portion of light from a first output and a second portion of light from a second output. As shown in FIG. 12, an electromagnetic waveguide 1206 (e.g., a single mode optical fiber, a polarization-maintaining single-mode optical fiber) can be optically coupled to a first output of fiber coupler 1204, and another electromagnetic waveguide 1208, can be optically coupled to a second output of fiber coupler 1204. In some embodiments, any suitable portion of the source light can be directed toward optical fiber 1206. For example, half of source light received at fiber coupler 1204 can be directed toward each of optical fiber 1206 and Alternatively, in some embodiments, polarization-maintaining optical fiber can be used to optically couple various components. For example, polarization-maintaining optical fiber can be used to optically couple phase modulator 1210 and polarization beam combiner 1218. As another example, polarization-maintaining optical fiber can be used to optically couple phase modulator 1212 and polarization beam combiner 1218. In some embodiments, polarization controller 1214 and/or polarization controller 1216 can be omitted (e.g., if polarization maintaining optical fiber is used to optically couple components).

In some embodiments, polarization controllers (e.g., polarization controller 1214 and/or polarization controller 1216) and/or polarization maintaining optical fiber can cause light traversing the two paths shown in FIG. 12 between fiber coupler 1204 and polarization beam combiner 1218 orthogonal at the polarization beam combiner 1218.

In some embodiments, light output by polarization beam combiner 1218 has a polarization that is a function of the phase of the light from the two paths (e.g., when the polarization between the light traversing the two paths shown in FIG. 12 between fiber coupler 1204 and polarization beam combiner 1218 is orthogonal).

In some embodiments, phase modulator 1210 and phase modulator 1212 can each be configured to induce a particular phase shift, and the polarization of light emitted by polarization beam combiner 1218 can be unaffected, but the phase of the output can be changed by a particular magnitude. For example, phase modulator 1210 and phase modulator 1212 can be configured to induce a 90 degree phase shift, which can be used to induce a 90 degree phase shift between reference arm light and sample arm light. However, this is merely an example, and phase modulator 1210 and phase modulator 1212 can be configured to induce a phase shift of any magnitude. Alternatively, phase modulator 1210 can be configured to induce a first phase shift and phase modulator 1212 can be configured to induce a second, different phase shift, different from the first phase shift, which can cause the light emitted by polarization beam combiner 1218 to be output in different polarization state relative to the state emitted when the phase modulators 1210 and 1212 do not induce the first and second phase shift. For example, phase modulator 1210 can be configured to induce a −90 degree phase shift and phase modulator 1212 can be configured to induce a positive 90 degree phase shift (or vice versa), which can cause the polarization of light emitted by polarization beam combiner 1218 to be output in an orthogonal state to that of the light emitted by polarization beam combiner 1218 without these phase shifts. However, this is merely an example, and phase modulator 1210 and phase modulator 1212 can be configured to induce a variety of polarization states.

In some embodiments, a phase modulator driver 1230 can provide drive signals to phase modulator 1210 and/or phase modulator 1212 to control the phase shift caused by the phase modulator. For example, phase modulator driver 1230 can provide drive signals to control the phase and/or polarization of light output by polarization beam combiner 1218. In a particular example, phase modulator driver 1230 can provide drive signals during a first period of time that cause a particular modulation (e.g., in phase and/or polarization), and can provide drive signals during a second period of time that cause a different modulation. In such an example, the first period of time can correspond to an A-line, part of an A-line, one or more pulses of a wavelength-stepped frequency comb source, etc., and the second period of time can correspond to a subsequent A-line, a different part of the A-line, one or more subsequent pulses of the wavelength-stepped frequency comb source, etc. Note that phase modulator driver 1230 can provide drive signals (or inhibit drive signals from being provided) to phase modulator 1210 and/or phase modulator 1212 to cause no modulation to be applied to the output by polarization beam combiner 1218.

In some embodiments, an output of polarization beam combiner 1218 can be optically coupled to an input of a fiber coupler 1220, which can pass a first portion of light to an optical fiber 1222 to be provided as output from components 1200. Fiber coupler 1220 can pass a second portion of light to an optical fiber 1224, which can be coupled to detector 1228 via a polarizer 1226. In some embodiments, an output of detector 1228 can be indicative of a polarization of light output by fiber coupler 1220, and can be used as feedback to phase modulator driver 1230 to maintain a consistent output from polarization beam combiner. For example, feedback from detector 1228 can be used by phase modulator driver 1230 to control phase drift of phase modulator 1210 and/or 1212. In some embodiments, fiber coupler 1220 can be configured to pass most of the light received at the input to optical fiber 1222 (e.g., over 50%, over 75%, over 85%, over 90%, etc.). In some embodiments, fiber coupler 1220, polarizer 1226, and detector 1228 can be omitted.

In some embodiments, polarization controllers can be positioned immediately prior to phase modulator 1210 and/or phase modulator 1212 (e.g., proximate to an input port of the phase modulator) to align the polarization of light input to the modulator to a specific orientation relative to the modulator. Additionally or alternatively, optical polarizers can be located proximate to fiber coupler 1204. For example, one optical polarizer can be positioned proximate to the input port of fiber coupler 1204. As another example, optical polarizers can be positioned proximate to the output ports of fiber coupler 1204 (e.g., one polarizer at each output port). As yet another example, optical polarizers can be positioned along optical fiber 1206 and optical fiber 1208. In such embodiments, the polarizer or set of polarizers can be used to eliminate variations in light polarization as a function of time or wavelength. In some embodiments, polarization controllers can be positioned before any one polarizer, or any combination of polarizers, to control the alignment of the input polarization state with the polarizer's axis.

Figure 13:
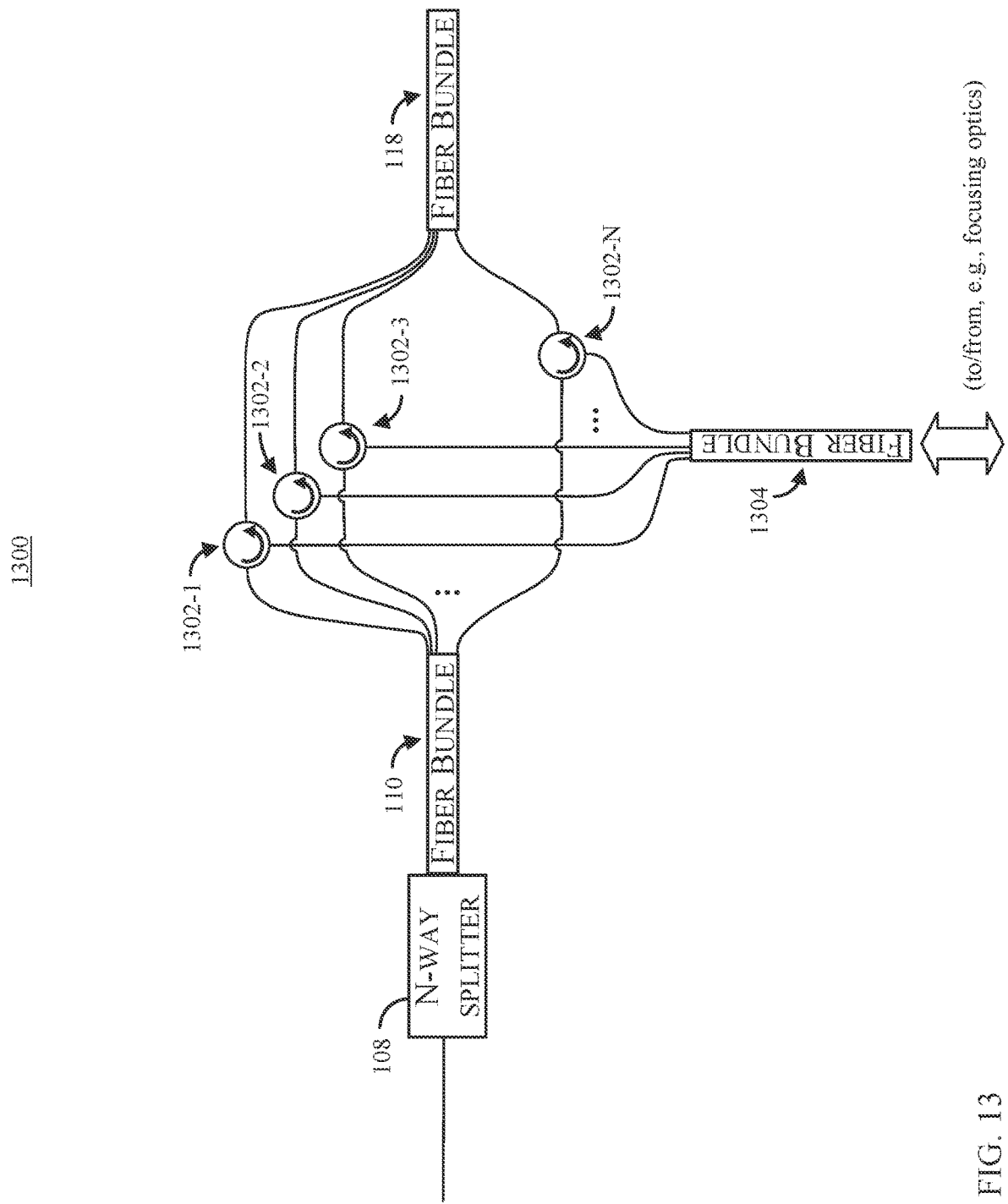
FIG. 13 shows an example of components that can be used to implement a portion of the sampling optics the system shown in FIG. 1 for multiple beam optical coherence tomography in accordance with some embodiments of the disclosed subject matter.

FIG. 13 shows an example 1300 of components that can be used to implement a portion of the sampling optics the system shown in FIG. 1 for multiple beam optical coherence tomography in accordance with some embodiments of the disclosed subject matter. In some embodiments, components 1300 can be used to couple fiber bundle 110 and fiber bundle 118 to a sample (e.g., via one or more other optical components). As shown in FIG. 13, N fibers of fiber bundle 110 (e.g., fibers of a ribbon fiber optic cable) can be individually coupled to a first port of optical circulators 1302-1 to 1302-N. In some embodiments, a second port of each optical circulator 1302 can be coupled to a respective optical fiber of fiber bundle 1304 (e.g., fibers of a ribbon fiber optic cable), which can convey light to and from a sample. A third port of optical circulator 1302 can be coupled to one of N fibers of fiber bundle 118 (e.g., fibers of a ribbon fiber optic cable), which can convey light received from the sample to a detector (e.g., detector 134 via mixer 130).

Figure 14:
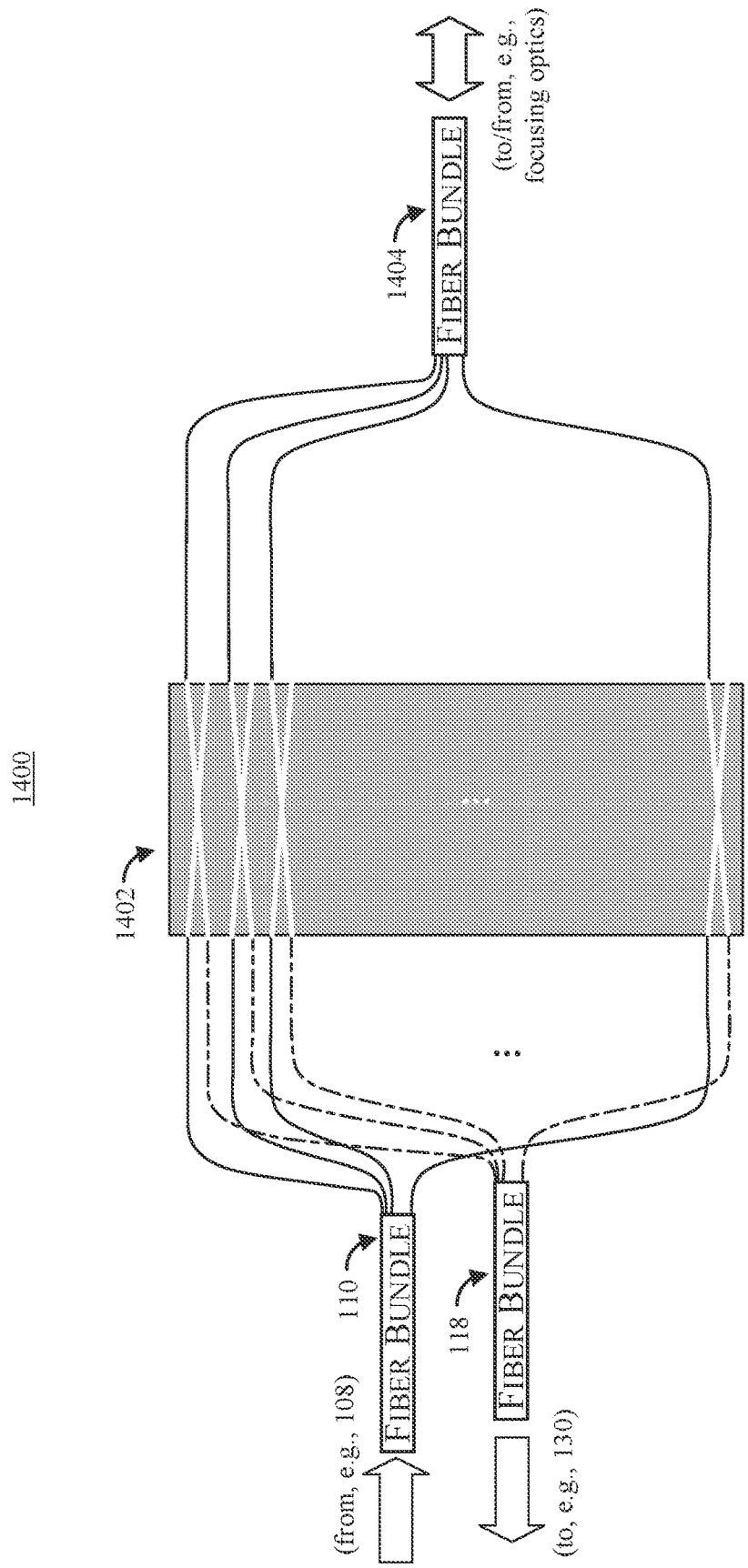
FIG. 14 shows another example of components that can be used to implement a portion of the sampling optics the system shown in FIG. 1 for multiple beam optical coherence tomography in accordance with some embodiments of the disclosed subject matter.

FIG. 14 shows another example 1400 of components that can be used to implement a portion of the sampling optics the system shown in FIG. 1 for multiple beam optical coherence tomography in accordance with some embodiments of the disclosed subject matter. In some embodiments, components 1400 can be used to couple fiber bundle 110 and fiber bundle 118 to a sample (e.g., via one or more other optical components). As shown in FIG. 14, N fibers of fiber bundle 110 (e.g., fibers of a ribbon fiber optic cable) can be individually coupled to a first port of a respective coupler, and N fibers of fiber bundle 118 (e.g., fibers of a ribbon fiber optic cable) can be individually coupled to a second port of the respective coupler. In some embodiments, N couplers can be implemented using a planar lightwave circuit (PLC) 1402. In some embodiments, N fibers of a fiber bundle 1404 (e.g., fibers of a ribbon fiber optic cable) can be individually coupled to a third port of the respective coupler. Fiber bundle 1404 can convey light to and from a sample, and light returned from the sample can be conveyed by respective couplers of PLC 1402 to fibers of fiber bundle 118, which can convey light received from the sample to a detector (e.g., detector 134 via mixer 130). In some embodiments, PLC 1402 can be configured to couple the first port of each coupler evenly to the third port and a fourth port, and to couple the third port of each coupler evenly to the first port and the second port. In such embodiments, half of the light output by fiber bundle 110 can be output to fibers of fiber bundle 1404, and half of the light from the sample that is output by fiber bundle 1404 can be output to fibers of fiber bundle 118.

Alternatively, in some embodiments, PLC 1402 can be configured to couple the first port of each coupler asymmetrically between the third port and the fourth port, and to couple the third port of each coupler asymmetrically between the first port and the second port. For example, PLC 1402 can be configured to couple less than half of the light output by fiber bundle 110 to fibers of fiber bundle 1404 (e.g., 1%, 5%, 10%, 20%, 25%, 30%, etc.). As another example, PLC 1402 can be configured to couple more than half of the light from the sample that is output by fiber bundle 1404 can be output to fibers of fiber bundle 118 (e.g., 99%, 95%, 90%, 80%, 75%, 70%, etc.). In such examples, the couplers of PLC 1402 can be configured to output light received at the first port to the fourth port and third port at a particular ratio (e.g., 99/1, 95/5, 90/10, etc.), and to output light received at the third port to the second port and first port at the same particular ratio. In some embodiments, configuring couplers of PLC 1402 to be asymmetric can reduce the optical loss of light transmitted by PLC 1402 between fibers of fiber bundle 1404 and fibers of fiber bundle 118. Note that although FIG. 14 shows N couplers implemented by PLC 1402, the couplers can be implemented using any suitable technique or combination of techniques. For example, discrete fiber connectors (e.g., similar to fiber connector 104) can be used to couple fiber bundle 110 to fiber bundle 1404 and to couple fiber bundle 1404 to fiber bundle 118.

Figure 15:
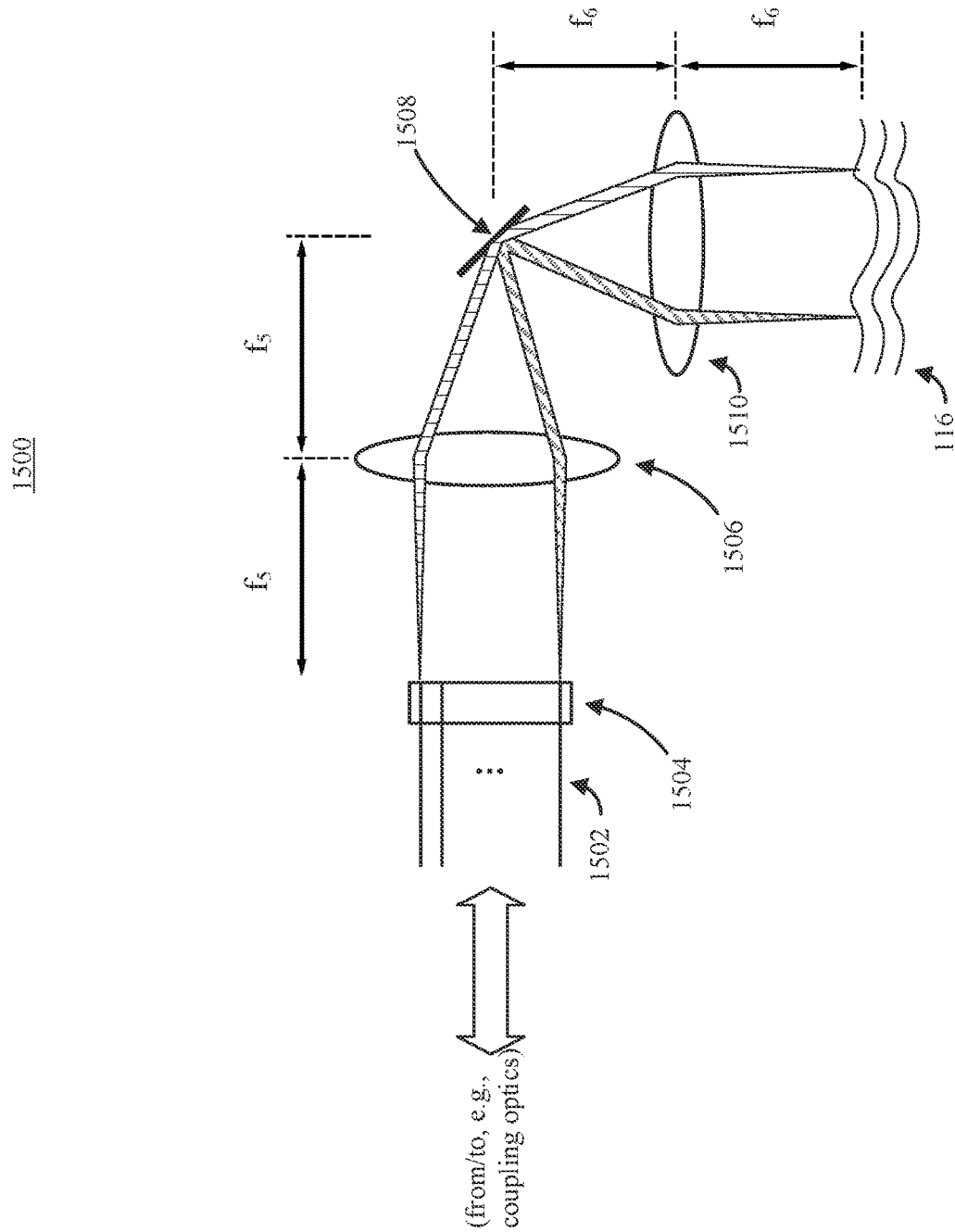
FIG. 15 shows another example of components that can be used to implement a focusing portion of the sampling optics the system shown in FIG. 1 for multiple beam optical coherence tomography in accordance with some embodiments of the disclosed subject matter.

FIG. 15 shows another example 1500 of components that can be used to implement a focusing portion of the sampling optics the system shown in FIG. 1 for multiple beam optical coherence tomography in accordance with some embodiments of the disclosed subject matter. In some embodiments, focusing optics 1500 can include a spatial separator 1504 that is configured to mechanically position the distal end of various optical fibers in an optical fiber bundle 1502 (e.g., fiber bundle 1304, fiber bundle 1404) such that a face of each optical fiber is held at a particular position and orientation relative to other optical components of focusing optics 1500. For example, the core of each individual optical fiber of optical fiber bundle 1502 can be positioned by placing the cladding surrounding the core into a v-shaped groove that is sized to precisely position an individual optical fiber including a core and cladding. Spatial separator 302 can position fibers at specific locations defined in 1 dimension (e.g., using a linear V-groove) or 2 dimensions (e.g., as an array). In some embodiments, spatial separator 1504 can be implemented using any suitable components. For example, spatial separator 1504 can be implemented as a V-groove assembly, such as a single-mode V-groove assembly available from OZ Optics headquartered in Ottawa, Canada. As another example, spatial separator 1504 can be implemented as an array of wells or through-holes in a material (e.g., glass, silicon-dioxide, etc.) into which individual fibers in a set of fibers can be fixed such that the face of each fiber is precisely aligned with respect to each other fiber. In such an example, such wells or through-holes can be generated mechanically (e.g., using mechanical drilling tools) and/or using other processes (e.g., photolithography). In such an example, the wells or through-holes of the array can be arranged in any suitable one dimensional or two dimensional layout (e.g., as a single row or column, as a set of rows or columns, as a series of concentric circles, etc.) As yet another example, spatial separator 1504 can be implemented as one or more multi-core fibers in which each optical core is arranged at a specific locations relative to each other optical core within the multi-core fiber.

In some embodiments, a first lens 1506 can be optically coupled to the optical fibers of fiber bundle 1502. As shown in FIG. 15, first lens 1506 can be arranged such that the face of each optical fiber of fiber bundle 1502 coincides with the focal length $f_5$ of first lens 1506, and emits a beam from a point that is a particular radial distance from the optical axis of first lens 1506. As shown in FIG. 15, first lens 1506 can be implemented as biconvex lens. However, this is merely an example, and many types of lens can be used to implement first lens 1506 (and other lenses shown in the drawings as biconvex lenses), such as lenses described above in connection with FIG. 3. In some embodiments, if spatial separator 1504 is used to arrange the optical fibers of fiber bundle 1502 in a straight line, such that the beams emitted by the optical fibers are all co-planar, spatial separator 1504 can be positioned with respect to first lens 1506 such that the optical axis of first lens 1506 is on the same plane as the beams. For example, this arrangement can facilitate alignment of one or more other components with spatial separator 1504 and first lens 1506.

In some embodiments, optical fibers of fiber bundle 1502 can emit an individual beam toward a first side of first lens 1506, which can focus the light received from optical bundle 1502 at focal length $f_5$ on a distal side of first lens 1506. This can cause the beams from each of the various optical fibers to converge at the focal point of first lens 1506. In the absence of other optical components, these beams would diverge again after the focal point such that at a distance $2*f_5$ from the face of the optical fibers the beams are mirrored across the optical axis and can be focused on a sample.

In some embodiments, focusing optics 1500 can include a reflector 1508 that redirects light received from first lens 1506 toward sample 116. Reflector 1508 can be arranged such that a reflecting surface of reflector 1508 coincides with the focal length $f_5$ of first lens 1506. In some embodiments, reflector 1508 can be implemented using any suitable reflective surface, such as a planar mirror, a galvanometer, a micro-electro-mechanical system (MEMS)-based mirror, a polygon mirror scanner, etc. In some embodiments, an angle of reflector 1508 can be fixed or adjustable. For example, in some embodiments, reflector 1508 can be a surface of a galvo scanner that can be used to control an angle that reflector 1508 makes with an optical axis of first lens 1506.

In some embodiments, beams emitted by first lens 1506 can converge at the reflective surface of reflector 1508, and can begin to diverge as the beams travel toward a first side of a second lens 1510. Second lens 1510 can be arranged such that the reflective surface of reflector 1508 coincides with a focal length $f_6$ of second lens 1510. In some embodiments, the focal length of second lens 1510 can be the same or different than the focal length of first lens 1506 (e.g., which can be the same or different than the focal length of first lens 304, second lens 308, third lens 312, and/or fourth lens 316).

In some embodiments, second lens 1510 can focus the diverging beams such that the beams form substantially parallel beams traveling parallel to the optical axis of second lens 1510 when the beams intersect a surface of sample 116. As shown in FIG. 15, in some embodiments, second lens 1510 can cause each beam to converge to a point at the focal length $f_6$. For example, when the reflective surface of reflector 1508 is placed at a distance equal to the focal length $f_6$ from the first side of second lens 1510, each beam can converge at a distance equal to the focal length $f_6$ on the second side of second lens 1510, and can begin diverging past the distance equal to the focal length $f_6$ (e.g., forming a beam waist at the focal length $f_6$).

In some embodiments, sample 116 can backscatter one or more portions of the light incident on the sample from each beam. The depth at which the light is backscattered can depend on the structure of sample 116 and/or the wavelength of the incident light. This can cause different amounts of phase shift between the backscattered light and light that traversed the reference arm. Additionally, light backscattered by sample 116 can have its polarization inverted.

In some embodiments, the light backscattered by sample 116 can traverse the same path through focusing optics 1500 as the incident light from light source 102 in reverse, such that a substantial portion of the backscattered light is directed on a path coinciding with spatial separator 1504, and conveyed back toward coupling optics along fiber bundle 1502.

In some embodiments, sampling optics 112 can be implemented using a combination of coupling optics 1300 and focusing optics 1500, or a combination of coupling optics 1400 and focusing optics 1500.

Figure 16:
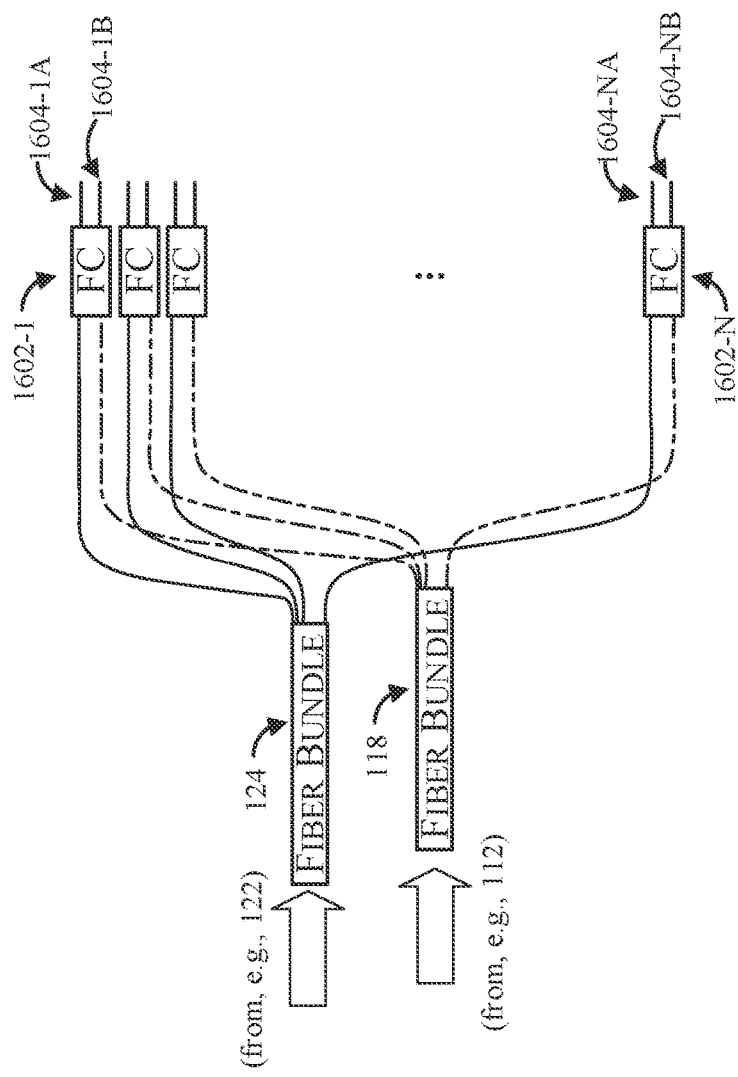
FIG. 16 shows an example of optical components that can be used to implement a mixing portion of a multi-beam interferometer for multiple beam optical coherence tomography in accordance with some embodiments of the disclosed subject matter.

FIG. 16 shows an example 1600 of optical components that can be used to implement a mixing portion of a multi-beam interferometer for multiple beam optical coherence tomography in accordance with some embodiments of the disclosed subject matter. In some embodiments, mixing components 1600 can combine light from N beams received from the sample arm and the reference arm. As shown in FIG. 16, N fibers of fiber bundle 118 (e.g., fibers of a ribbon fiber optic cable) can be individually coupled to a first port of a respective fiber coupler 1602, and N fibers of fiber bundle 124 (e.g., fibers of a ribbon fiber optic cable) can be individually coupled to a second port of the respective fiber coupler 1602. For example, in some embodiments, a first fiber from fiber bundle 118 can be optically coupled to a first port of fiber coupler 1602-1, and a corresponding first fiber from fiber bundle 124 can be optically coupled to a second port of fiber coupler 1602-1.

In some embodiments, N couplers can be implemented using N individual fiber couplers 1602. In some embodiments, a first fiber (e.g., fiber 1604-1A) can be optically coupled to a third port of each fiber coupler 1602 and a second fiber (e.g., fiber 1604-1B) can be optically coupled to a fourth port of each fiber coupler 1602. Fiber 1604-1A and fiber 1604-1B can convey interference fringes to a detector (e.g., detector 134). For example, fiber 1604-1A can optically couple the third port of fiber coupler 1602-1 to a first port of a balanced detector (e.g., balanced detector 520-1), and fiber 1604-1B can optically couple the third port of fiber coupler 1602-1 to a second port of the balanced detector. Similarly, two fibers can be used to optically couple the third and fourth ports of each of the other N−1 fiber couplers 1602 to a detector (e.g., a balanced detector). Note that in general the fringes output on each port of a particular fiber coupler 1602 initially have the same polarization and are 180 degrees out of phase. As the light propagates from fiber coupler 1602 the polarization in each fiber may diverge (e.g., for single mode fibers, a polarization of the light in fiber 1604-1A may diverge from a polarization of the light in fiber 1604-1B), while the phase relationship between the two fringe signals is generally maintained. This can facilitate suppression of a DC-noise component, and can amplify the signal encoded in the fringe using a balanced detector.

In some embodiments, balanced detectors can be omitted. For example, as described above in connection with FIG. 5, a balanced detection operation can be implemented digitally (e.g., in lieu of using balanced detectors 520). For example, single detectors (e.g., a single photodetector) can be optically coupled to each fiber coupler 1602 (e.g., in lieu of balanced detectors 520). In such an example, one or more beams from fiber bundle 124 can be optically coupled to a single detector without being mixed with a corresponding beam from fiber bundle 118, such that at least one fiber 1604 (e.g., 1604-NA) conveys only reference arm light (e.g., with other fibers 1604 conveying fringe signals). In such an example, fibers 1604-1B to 1604-NB can be omitted. In a more particular example, one or more fiber from fiber bundle 118 are not optically coupled to detector 134 via mixer 130. As another more particular example, fiber bundle 124 can include more fibers than fiber bundle 118, such that the reference arm has more beams than the sample arm. As yet another more particular example, in addition to or in lieu of the previous examples, a portion of light output by light source 102 (e.g., 1%, 2%, etc.) can be directed to one or more reference detectors without passing through the reference arm or sample arm to provide a signal that is substantially similar to reference arm signals in fiber bundle 124. One or more detectors (e.g., reference detectors) can be optically coupled to a fiber/waveguide of fiber bundle 124 that includes only reference arm light, and can be used to record the intensity of the reference arm light concurrently with other detectors recording intensity of fringe signals (e.g., fringe detectors). A digitized signal from the reference detector can be subtracted from digitized signals from the fringe detectors to remove noise (e.g., noise caused by fluctuations in laser power) fringe signals digitized on the remaining detectors.

In some embodiments, approximately half of the light received at the first port of each fiber coupler 1602 can be output on the third port and fourth port of fiber coupler 1602, and approximately half of the light received at the second port of each fiber coupler 1602 can be output on the third port and fourth port of fiber coupler 1602. In such embodiments, light from the sample arm and the reference arm can mix within fiber coupler 1602, generating fringes that are output on the third port and fourth port of fiber coupler 1602.

Figure 17:
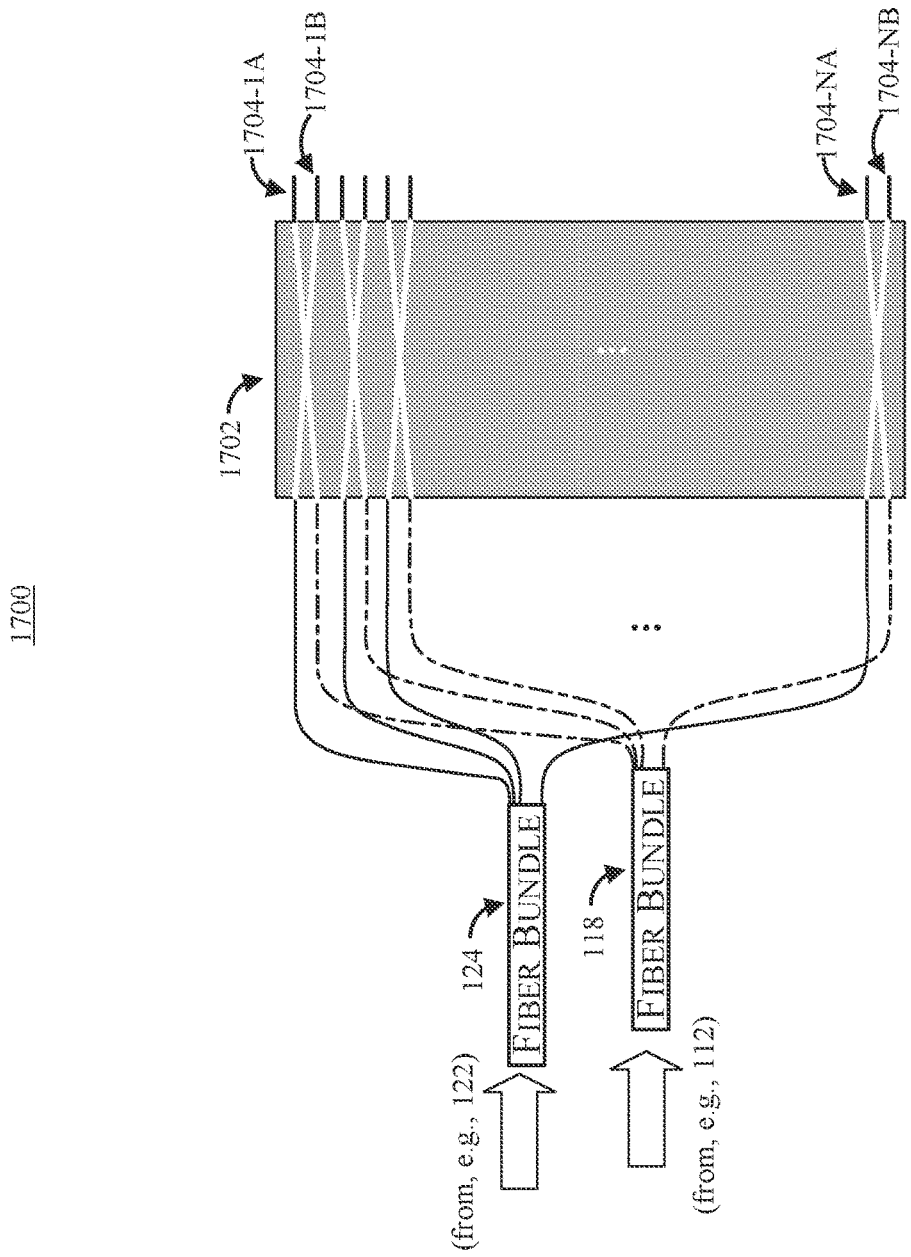
FIG. 17 shows another example of optical components that can be used to implement a mixing portion of a multi-beam interferometer for multiple beam optical coherence tomography in accordance with some embodiments of the disclosed subject matter.

FIG. 17 shows another example 1700 of optical components that can be used to implement a mixing portion of a multi-beam interferometer for multiple beam optical coherence tomography in accordance with some embodiments of the disclosed subject matter.

In some embodiments, mixing components 1700 can combine light from N beams received from the sample arm and the reference arm. As shown in FIG. 17, N fibers of fiber bundle 118 (e.g., fibers of a ribbon fiber optic cable) can be individually coupled to a first port of a respective coupler implemented using a PLC 1702, and N fibers of fiber bundle 124 (e.g., fibers of a ribbon fiber optic cable) can be individually coupled to a second port of the respective fiber coupler implemented using PLC 1702.

In some embodiments, PLC 1702 can implement N couplers. In some embodiments, a first fiber (e.g., fiber 1704-1A) can be optically coupled to a third port of each coupler of PLC 1702 and a second fiber (e.g., fiber 1704-1B) can be optically coupled to a fourth port of each coupler of PLC 1702. Fiber 1704-1A and fiber 1704-1B can convey interference fringes to a detector (e.g., detector 134). For example, fiber 1704-1A can optically couple the third port of a first coupler of PLC 1702 to a first port of a balanced detector (e.g., balanced detector 520-1), and fiber 1704-1B can optically couple the third port of the first coupler of PLC 1702 to a second port of the balanced detector. Similarly, two fibers can be used to optically couple the third and fourth ports of each of the other N−1 couplers of PLC 1702 to a detector (e.g., a balanced detector). Alternatively, as described above in connection with FIG. 16, a balanced detection operation can be implemented digitally (e.g., in lieu of using balanced detectors 520).

In some embodiments, approximately half of the light received at the first port of each coupler of PLC 1702 can be output on the third port and fourth port of the coupler, and approximately half of the light received at the second port of each coupler of PLC 1702 can be output on the third port and fourth port of fiber coupler 1702. In such embodiments, light from the sample arm and the reference arm can mix within the coupler, generating fringes that are output on the third port and fourth port of the coupler.

FURTHER EXAMPLES HAVING A VARIETY OF FEATURES

Example 1: A system for multiple beam optical coherence tomography, comprising: a sample arm optically configured to be coupled to a light source, the sample arm comprising: a first optical fiber comprising a proximal end optically coupled to the light source and a distal end, a first splitter optically coupled to the distal end of the first optical fiber and optically coupled to a proximal end of each of a first plurality of optical fibers, wherein the first plurality of optical fibers comprises n optical fibers, and a first plurality of optical components configured to: receive from the plurality of optical fibers a respective plurality of beams, cause the plurality of beams to be emitted toward a sample, receive a plurality of backscattered light samples from the sample, wherein the plurality of backscattered light samples are spatially separated, and wherein each of the plurality of backscattered light samples corresponds to one of the first plurality of beams, and direct the plurality of backscattered light samples toward a detector; a reference arm optically coupled to the light source, the reference arm comprising: a second optical fiber comprising a proximal end optically coupled to the light source and a distal end, and a second splitter optically coupled to the distal end of the second optical fiber and optically coupled to a proximal end of each of a second plurality of optical fibers, wherein the second plurality of optical fibers comprises n optical fibers; a second plurality of optical components configured to: combine each of the plurality of backscattered light samples with a beam emitted by a corresponding optical fiber of the second plurality of optical fibers yielding a plurality of fringes, and direct each of the plurality of fringes to a corresponding channel of the detector; and the detector comprising a plurality of detection channels, the detector configured to output optical coherence tomography data indicative of a structure of the sample at a plurality of locations that generated the plurality of backscattered light samples.

Example 2: The system of Example 1, wherein the light source is a wavelength-swept laser.

Example 3: The system of Example 1, wherein the light source is a wavelength-stepped frequency comb source.

Example 4: The system of any one of Examples 1-3, wherein the sample arm further comprises: a first spatial separator mechanically coupled to a distal end of each optical fiber of the first plurality of optical fibers.

Example 5: The system of Example 4, wherein the first spatial separator comprises a V-groove assembly.

Example 6: The system of any one of Examples 1-5, wherein the reference arm further comprises: a second spatial separator mechanically coupled to a distal end of each optical fiber of the second plurality of optical fibers.

Example 7: The system of any one of Examples 1-6, wherein the particular spectral range is centered at 1300 nanometers.

Example 8: The system of any one of Examples 1-7, wherein the first splitter comprises a planar lightwave circuit splitter that receives light from the first optical fiber and splits the received light into outputs.

Example 9: The system of any one of Examples 1-8, wherein the first plurality of optical components comprises: a first lens having a first side optically coupled to the first plurality of optical fibers and a second side, wherein the first lens is configured to focus the plurality of beams at a first focal distance corresponding to a focal length of the first lens; a surface configured to redirect light received from the second side of the first lens toward a first side of a second lens and redirect light received from the first side of the second lens toward the second side of the first lens; the second lens having the first side optically coupled to the surface and a second side configured to direct light received from the surface toward the sample and receive the plurality of backscattered light samples from the sample.

Example 10: The system of Example 9, wherein the first plurality of optical components comprises: a third lens having a first side optically coupled to the first plurality of optical fibers and a second side, wherein the third lens is configured to focus the plurality of beams at a first focal distance corresponding to a focal length of the third lens; a polarizing beam splitter comprising a first port, a second port, and a third port and a first interface that passes light having a first polarization and redirects light having a second polarization, wherein the beam splitter is configured to pass light having the first polarization received at the first port to the second port and redirect light having the second polarization received at the second port toward the third port, wherein the first port is optically coupled to the second side of the third lens such that the first port receives the plurality of beams from the third lens, wherein the second port is optically coupled to a first side of a fourth lens such that the second port emits the plurality of beams toward the fourth lens and receives the plurality of backscattered samples from the fourth lens, and wherein the third port is configured to emit the plurality of samples toward a fifth lens; the fourth lens having the first side optically coupled to the second port and having a second side; a quarter wave plate optically coupled to the second side of the fourth lens and a first side of the first lens, wherein the first side of the first lens is optically coupled to the quarter wave plate; and the fifth lens having a first side optically coupled to the third port of the polarizing beam splitter and a second side optically coupled to a third plurality of optical fibers, wherein the first plurality of optical fibers and the third plurality of optical fibers are oriented such that light emitted from the first plurality of optical fibers is transmitted to respective optical fibers of the third plurality of optical fibers.

Example 11: The system of any one of Examples 1-9, wherein the first plurality of optical components comprises: a plurality of optical circulators, each of the optical circulators having a first port, a second port, and a third port, wherein the first port of each of the plurality of optical circulators is optically coupled to the light source via a respective optical fiber of the first plurality of optical fibers, the second port of each of the plurality of optical circulators is optically coupled to the sample via a respective optical fiber of a third plurality of optical fibers, and the third port of each of the plurality of optical circulators is optically coupled to the second plurality of optical components via a respective optical fiber of a fourth plurality of optical fibers.

Example 12: The system of any one of Examples 1-9, wherein the first plurality of optical components comprises: a second planar lightwave circuit comprising a plurality of optical couplers, each having a first port, a second port, and a third port, wherein the first port of each of the plurality of optical couplers is optically coupled to the light source via a respective optical fiber of the first plurality of optical fibers, the second port of each of the plurality of optical couplers is optically coupled to the sample via a respective optical fiber of a third plurality of optical fibers, and the third port of each of the plurality of optical couplers is optically coupled to the second plurality of optical components via a respective optical fiber of a fourth plurality of optical fibers.

Example 13: The system of Example 12, wherein each of the plurality of optical couplers is configured to: output, from the third port, a first fraction of light received at the first port; output, from a fourth port, a second fraction of light received at the first port; output, from the first port, the first fraction of light received at the third port; and output, from the second port, the second fraction of light received at the third port.

Example 14: The system of Example 13, wherein a ratio between the first fraction and the second fraction is approximately equal to one.

Example 15: The system of Example 14, wherein a ratio between the first fraction and the second fraction is less than one.

Example 16: The system of any one of Examples 10-15, further comprising a spatial separator mechanically coupled to a distal end of each optical fiber of the third plurality of optical fibers, and disposed to optically couple each optical fiber of the third plurality of optical fibers to the first side of the first lens.

Example 17: The system of any one of Examples 1-16, wherein the second plurality of optical components comprises a beam splitter comprising a first port, a second port, and a third port, wherein the first port is configured to receive light emitted by the second plurality of optical, wherein the second port is configured to receive the plurality of backscattered light samples, and wherein the third port is configured to output the plurality of fringes.

Example 18: The system of Example 17, wherein the detector comprises a plurality of balanced detectors comprising a first port and a second port, each of the plurality of balanced detectors corresponding to a respective channel of the detector, wherein the beam splitter further comprises a fourth port configured to output a second plurality of fringes, and wherein each of the plurality of balanced detectors receives a fringe of the plurality of fringes and a corresponding fringe of the second plurality of fringes, and outputs a signal based on both fringes.

Example 19: The system of any one of Examples 1-16, wherein the second plurality of optical components comprises: a plurality of optical couplers, each having a first port, a second port, a third port, and a fourth port, wherein the first port is coupled to the light source via a respective optical fiber of the second plurality of optical fibers; the second port is coupled to the sample via a respective optical fiber of a plurality fourth plurality of optical fibers; the third port is coupled to a respective channel of the plurality of detection channels; and the fourth port is coupled to the respective channel of the plurality of detection channels.

Example 20: The system of Example 19, wherein each of the plurality of optical couplers is a discrete fiber coupler.

Example 21: The system of Example 19, further comprising a third planar lightwave circuit, wherein the planar lightwave circuit comprises the plurality of optical couplers.

Example 22: The system of any one of Examples 1-21, wherein the reference arm further comprises a modulation component disposed between the light source and the second splitter, the modulation component configured to modulate at least polarization of light provided to the second splitter.

Example 23: The system of any one of Examples 1-22, wherein the reference arm further comprises a modulation component disposed between the light source and the second splitter, the modulation component configured to modulate at least a phase of light provided to the second splitter.

Example 24: The system of any one of Example 1, wherein the reference arm further comprises a modulation component disposed between the light source and the second splitter, the modulation component configured to: modulate a phase of light provided to the second splitter; and modulate polarization of light provided to the second splitter.

Example 25: The system of any one of Examples 1-24, wherein the sample arm further comprises a modulation component disposed between the light source and the first splitter, the modulation component configured to modulate at least polarization of light provided to the first splitter.

Example 26: The system of any one of Examples 1-25, wherein the sample arm further comprises a modulation component disposed between the light source and the first splitter, the modulation component configured to modulate at least a phase of light provided to the first splitter.

Example 27: The system of and one of Examples 1-24, wherein the sample arm further comprises a modulation component disposed between the light source and the first splitter, the modulation component configured to: modulate a phase of light provided to the first splitter; and modulate polarization of light provided to the first splitter.

Example 28: The system of any one of Examples 22 to 27, wherein the modulation component comprises: a coupler comprising: a first port optically coupled to the light source; a second port; and a third port; a first phase modulator comprising: a first port optically coupled to the second port of the coupler; and a second port; a second phase modulator comprising: a first port optically coupled to the third port of the coupler; and a second port; and a beam combiner comprising: a first port optically coupled to the first phase modulator; a second port optically coupled to the second phase modulator; and a third port.

Example 29: The system of Example 28, wherein the modulation component further comprises: a polarization controller optically coupled to the second port of the coupler and the first port of the first phase modulator.

Example 30: The system of any one of Examples 28 or 29, wherein the modulation component further comprises: a polarization controller optically coupled to the third port of the coupler and the sport of the second phase modulator.

Example 31: A system for multiple beam optical coherence tomography, comprising: a first splitter arranged to receive first light from a light source and output a fraction of the first light to each of a first plurality of waveguides; optical components arranged to: receive light from the first plurality of waveguides; direct the received light as a plurality of beams toward a sample such that each of the plurality of beams impinges the sample at a different lateral position; and collect a plurality of backscattered light samples from the different lateral positons of the sample; a second splitter arranged to receive second light from the light source and output a fraction of the second light to each of a second plurality of waveguides as a plurality of reference light samples; a mixer arranged to receive the plurality of backscattered light samples and the plurality of reference light samples and combine each backscattered light sample with a corresponding reference light sample such that the mixer outputs a plurality of fringes; and a detector arranged to receive the plurality of fringes and output a plurality of optical coherence tomography signals, wherein each of the plurality of optical coherence tomography signals is indicative of a structure of the sample at a respective lateral position.

Example 32: The system of Example 31, wherein the plurality of beams comprises eight beams.

Example 33: The system of any one of Examples 31 or 32, wherein the first splitter comprises a planar lightwave circuit splitter.

Example 34: The system of any one of Examples 31 to 33, wherein the optical components comprise: a plurality of optical circulators, each of the plurality of optical circulators arranged to: receive a beam of the plurality of beams from a waveguide of the first plurality of waveguides; direct the received beam toward the sample; and direct a backscattered light sample toward the detector.

Example 35: The system of any one of Examples 31 to 33, wherein the optical components comprise: a plurality of optical couplers, each of the plurality of optical circulators arranged to: receive a beam of the plurality of beams from a waveguide of the first plurality of waveguides; direct the received beam toward the sample; and direct a backscattered light sample toward the detector.

Example 36: The system of any one of Examples 31 to 35, further comprising the light source.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A system for multiple beam optical coherence tomography, comprising:
    a sample arm optically configured to be coupled to a light source, the sample arm comprising:
        a first optical fiber comprising a proximal end optically coupled to the light source and a distal end,
        a first splitter optically coupled to the distal end of the first optical fiber and optically coupled to a proximal end of each of a first plurality of optical fibers, wherein the first plurality of optical fibers comprises n optical fibers, and
        a first plurality of optical components configured to:
            receive from the plurality of optical fibers a respective plurality of beams,
            cause the plurality of beams to be emitted toward a sample,
            receive a plurality of backscattered light samples from the sample,
                wherein the plurality of backscattered light samples are spatially separated, and
                wherein each of the plurality of backscattered light samples corresponds to one of the plurality of beams, and
            direct the plurality of backscattered light samples toward a detector;
    a reference arm optically coupled to the light source, the reference arm comprising:
        a second optical fiber comprising a proximal end optically coupled to the light source and a distal end, and
        a second splitter optically coupled to the distal end of the second optical fiber and optically coupled to a proximal end of each of a second plurality of optical fibers, wherein the second plurality of optical fibers comprises n optical fibers;
    a second plurality of optical components configured to:
        combine each of the plurality of backscattered light samples with a beam emitted by a corresponding optical fiber of the second plurality of optical fibers yielding a plurality of fringes, and
        direct each of the plurality of fringes to a corresponding channel of the detector,
            the second plurality of optical components comprising a beam splitter comprising a first port, a second port, and a third port,
            the first port being configured to receive light emitted by the second plurality of optical components,
            the second port being configured to receive the plurality of backscattered light samples, and
            the third port being configured to output the plurality of fringes; and
    the detector comprising a plurality of detection channels, the detector configured to output optical coherence tomography data indicative of a structure of the sample at a plurality of locations that generated the plurality of backscattered light samples,
    the detector comprising a plurality of balanced detectors comprising a first port and a second port, each of the plurality of balanced detectors corresponding to a respective channel of the detector,
    the beam splitter further comprising a fourth port configured to output a second plurality of fringes, and
    each of the plurality of balanced detectors receiving a fringe of the plurality of fringes and a corresponding fringe of the second plurality of fringes and outputting a signal based on both fringes.

2. The system of claim 1, wherein the light source is a wavelength-swept laser.

3. The system of claim 1, wherein the light source is a wavelength-stepped frequency comb source.

4. The system of claim 1, wherein the sample arm further comprises:
    a first spatial separator mechanically coupled to a distal end of each optical fiber of the first plurality of optical fibers.

5. The system of claim 4, wherein the first spatial separator comprises a V-groove assembly.

6. The system of claim 1, wherein the reference arm further comprises:
    a second spatial separator mechanically coupled to a distal end of each optical fiber of the second plurality of optical fibers.

7. The system of claim 1, wherein the light source emits light in a spectral range centered on 1300 nanometers.

8. The system of claim 1, wherein the first splitter comprises a planar lightwave circuit splitter that receives light from the first optical fiber and splits the received light into n outputs.

9. The system of claim 1, wherein the first plurality of optical components comprises:
a first lens having a first side optically coupled to the first plurality of optical fibers and a second side, wherein the first lens is configured to focus the plurality of beams at a first focal distance corresponding to a focal length of the first lens;
a surface configured to redirect light received from the second side of the first lens toward a first side of a second lens and redirect light received from the first side of the second lens toward the second side of the first lens; and
the second lens having the first side optically coupled to the surface and a second side configured to direct light received from the surface toward the sample and receive the plurality of backscattered light samples from the sample.

10. The system of claim 9, wherein the first plurality of optical components comprises:
a third lens having a first side optically coupled to the first plurality of optical fibers and a second side, wherein the third lens is configured to focus the plurality of beams at a first focal distance corresponding to a focal length of the third lens;
a polarizing beam splitter comprising a first port, a second port, and a third port and a first interface that passes light having a first polarization and redirects light having a second polarization,
wherein the beam splitter is configured to pass light having the first polarization received at the first port to the second port and redirect light having the second polarization received at the second port toward the third port,
wherein the first port is optically coupled to the second side of the third lens such that the first port receives the plurality of beams from the third lens,
wherein the second port is optically coupled to a first side of a fourth lens such that the second port emits the plurality of beams toward the fourth lens and receives the plurality of backscattered light samples from the fourth lens, and
wherein the third port is configured to emit the plurality of backscattered light samples toward a fifth lens;
the fourth lens having the first side optically coupled to the second port and having a second side;
a quarter wave plate optically coupled to the second side of the fourth lens and a first side of the first lens,
wherein the first side of the first lens is optically coupled to the quarter wave plate; and
the fifth lens having a first side optically coupled to the third port of the polarizing beam splitter and a second side optically coupled to a third plurality of optical fibers,
wherein the first plurality of optical fibers and the third plurality of optical fibers are oriented such that light emitted from the first plurality of optical fibers is transmitted to respective optical fibers of the third plurality of optical fibers.

11. The system of claim 10, further comprising a spatial separator mechanically coupled to a distal end of each optical fiber of the third plurality of optical fibers, and disposed to optically couple each optical fiber of the third plurality of optical fibers to the first side of the first lens.

12. The system of claim 1, wherein the first plurality of optical components comprises:
a plurality of optical circulators, each of the optical circulators having a first port, a second port, and a third port,
wherein the first port of each of the plurality of optical circulators is optically coupled to the light source via a respective optical fiber of the first plurality of optical fibers,
the second port of each of the plurality of optical circulators is optically coupled to the sample via a respective optical fiber of a third plurality of optical fibers, and
the third port of each of the plurality of optical circulators is optically coupled to the second plurality of optical components via a respective optical fiber of a fourth plurality of optical fibers.

13. The system of claim 1, wherein the first plurality of optical components comprises:
a second planar lightwave circuit comprising a plurality of optical couplers, each having a first port, a second port, and a third port,
wherein the first port of each of the plurality of optical couplers is optically coupled to the light source via a respective optical fiber of the first plurality of optical fibers,
the second port of each of the plurality of optical couplers is optically coupled to the sample via a respective optical fiber of a third plurality of optical fibers, and
the third port of each of the plurality of optical couplers is optically coupled to the second plurality of optical components via a respective optical fiber of a fourth plurality of optical fibers.

14. The system of claim 13, wherein each of the plurality of optical couplers is configured to:
output, from the third port, a first fraction of light received at the first port;
output, from a fourth port, a second fraction of light received at the first port;
output, from the first port, the first fraction of light received at the third port; and
output, from the second port, the second fraction of light received at the third port.

15. The system of claim 14, wherein a ratio between the first fraction and the second fraction is approximately equal to one.

16. The system of claim 14, wherein a ratio between the first fraction and the second fraction is less than one.

17. The system of claim 1, wherein the reference arm further comprises a modulation component disposed between the light source and the second splitter, the modulation component configured to modulate at least polarization of light provided to the second splitter.

18. The system of claim 17, wherein the modulation component comprises:
a coupler comprising:
a first port optically coupled to the light source;
a second port; and
a third port;
a first phase modulator comprising:
a first port optically coupled to the second port of the coupler; and
a second port;

a second phase modulator comprising:
  a first port optically coupled to the third port of the coupler; and
  a second port; and
a beam combiner comprising:
  a first port optically coupled to the first phase modulator;
  a second port optically coupled to the second phase modulator; and
  a third port.

19. The system of claim 18, wherein the modulation component further comprises:
  a polarization controller optically coupled to the second port of the coupler and the first port of the first phase modulator.

20. The system of claim 18, wherein the modulation component further comprises:
  a polarization controller optically coupled to the third port of the coupler and the second port of the second phase modulator.

21. The system of claim 1, wherein the second plurality of optical components comprises:
  a plurality of optical couplers, each having a first port, a second port, a third port, and a fourth port,
    wherein the first port is coupled to the light source via a respective optical fiber of the second plurality of optical fibers;
    the second port is coupled to the sample via a respective optical fiber of a plurality fourth plurality of optical fibers;
    the third port is coupled to a respective channel of the plurality of detection channels; and
    the fourth port is coupled to the respective channel of the plurality of detection channels.

22. The system of claim 21, further comprising a third planar lightwave circuit, wherein the third planar lightwave circuit comprises the plurality of optical couplers.

23. The system of claim 1, wherein the reference arm further comprises a modulation component disposed between the light source and the second splitter, the modulation component configured to modulate at least a phase of light provided to the second splitter.

24. The system of claim 1, wherein the sample arm further comprises a modulation component disposed between the light source and the first splitter, the modulation component configured to modulate at least a phase of light provided to the first splitter.

25. The system of claim 1, wherein the sample arm further comprises a modulation component disposed between the light source and the first splitter, the modulation component configured to modulate at least polarization of light provided to the first splitter.

26. A system for multiple beam optical coherence tomography, comprising:
  a first splitter arranged to receive first light from a light source and output a fraction of the first light to each of a first plurality of waveguides;
  optical components arranged to:
    receive light from the first plurality of waveguides;
    direct the received light as a plurality of beams toward a sample such that each of the plurality of beams impinges the sample at a different lateral position; and
    collect a plurality of backscattered light samples from the different lateral positions of the sample;
  a second splitter arranged to receive second light from the light source and output a fraction of the second light to each of a second plurality of waveguides as a plurality of reference light samples;
  a mixer arranged to receive the plurality of backscattered light samples and the plurality of reference light samples and combine each backscattered light sample with a corresponding reference light sample such that the mixer outputs a plurality of fringes,
    the first splitter comprising a planar lightwave circuit splitter comprising a plurality of optical couplers, each having a first port, a second port, and a third port,
      the first port of each of the plurality of optical couplers being optically coupled to the light source,
      the second port of each of the plurality of optical couplers being optically coupled to the sample, and
      the third port of each of the plurality of optical couplers being optically coupled to the mixer; and
  a detector arranged to receive the plurality of fringes and output a plurality of optical coherence tomography signals,
    each of the plurality of optical coherence tomography signals being indicative of a structure of the sample at a respective lateral position.

27. The system of claim 26, wherein the plurality of beams comprises eight beams.

28. The system of claim 26, wherein the optical components comprise:
  a plurality of optical circulators, each of the plurality of optical circulators arranged to:
    receive a beam of the plurality of beams from a waveguide of the first plurality of waveguides;
    direct the received beam toward the sample; and
    direct a backscattered light sample toward the detector.

29. The system of claim 26, wherein the optical components comprise:
  a plurality of optical couplers, each of the plurality of optical couplers arranged to:
    receive a beam of the plurality of beams from a waveguide of the first plurality of waveguides;
    direct the received beam toward the sample; and
    direct a backscattered light sample toward the detector.

* * * * *